United States Patent
Brandan et al.

(10) Patent No.: US 11,299,537 B2
(45) Date of Patent: Apr. 12, 2022

(54) METHODS FOR TREATMENT OF MOTOR NEURON DISEASES

(71) Applicant: FibroGen, Inc., San Francisco, CA (US)

(72) Inventors: Enrique Brandan, Santiago (CL); David Gonzalez, Santiago (CL)

(73) Assignee: FIBROGEN, INC., San Francisco, CA (US)

( * ) Notice: Subject to any disclaimer, the term of this patent is extended or adjusted under 35 U.S.C. 154(b) by 0 days.

(21) Appl. No.: 16/060,301

(22) PCT Filed: Dec. 6, 2016

(86) PCT No.: PCT/US2016/065153
§ 371 (c)(1),
(2) Date: Jun. 7, 2018

(87) PCT Pub. No.: WO2017/100193
PCT Pub. Date: Jun. 15, 2017

(65) Prior Publication Data
US 2019/0002547 A1    Jan. 3, 2019

Related U.S. Application Data

(60) Provisional application No. 62/336,168, filed on May 13, 2016, provisional application No. 62/265,704, filed on Dec. 10, 2015.

(51) Int. Cl.
| | | |
|---|---|---|
| *A61P 25/28* | (2006.01) | |
| *C07K 16/22* | (2006.01) | |
| *C07K 14/475* | (2006.01) | |
| *A61K 31/428* | (2006.01) | |
| *A61K 31/7088* | (2006.01) | |
| *A61K 39/00* | (2006.01) | |

(52) U.S. Cl.
CPC ............ *C07K 16/22* (2013.01); *A61K 31/428* (2013.01); *A61K 31/7088* (2013.01); *A61P 25/28* (2018.01); *C07K 14/475* (2013.01); *A61K 2039/505* (2013.01); *C07K 2317/21* (2013.01); *Y02A 50/30* (2018.01)

(58) Field of Classification Search
None
See application file for complete search history.

(56) References Cited

U.S. PATENT DOCUMENTS

| | | |
|---|---|---|
| 8,461,326 B2 | 6/2013 | Khvorova |
| 2004/0248206 A1 | 12/2004 | Lin et al. |
| 2006/0002913 A1 | 1/2006 | Gehlsen |
| (Continued) | | |

OTHER PUBLICATIONS

Anand et al., ALS and Oxidative Stress: The Neurovascular Scenario. Oxidative Medicine and Cellular Longevityvol. 2013, Article ID 635831, 14 (Year: 2013).*

(Continued)

*Primary Examiner* — Aurora M Fontainhas
(74) *Attorney, Agent, or Firm* — Leanne C. Price, Esq.

(57) ABSTRACT

The invention relates to methods and agents useful for treating motor neuron diseases (MNDs), in particular, amyotrophic lateral sclerosis (ALS). Methods and agents for treating various physiological and pathological conditions associated with motor neuron diseases are also provided.

8 Claims, 12 Drawing Sheets

(56) References Cited

U.S. PATENT DOCUMENTS

2012/0164151 A1* 6/2012 Brandan .............. A61P 21/00
                                                       424/145.1
2015/0148329 A1   5/2015 Reitz et al.

OTHER PUBLICATIONS

Schmidt et al., Neurodegenerative Diseases of the Retina and Potential for Protection and Recovery.Curr Neuropharmacol. Jun. 2008; 6(2): 164-178 (Year: 2008).*
McClain et al., Increased MMP-3 and CTGF expression during lipopolysaccharide-induced dopaminergic neurodegeneration. Neuroscience Letters vol. 460, 1, Aug. 2009, p. 27-31 (Year: 2009).*
International Search Report for PCT/US 16/65153.
Spliet WG, et al. "Increased Expression of Connective Tissue Growth Factor in Amyotrophic Lateral Sclerosis Human Spinal Cord" Acta Neuropathol, Nov. 2003; 106(5):449-67.
Rebolledo DL et al. "Fibrosis Associated to Skeletal Muscle Devernation and to Amyotrophic Lateral Sclerosis (ALS) Model: Role of CTGF/CCN2" 8th International Workshop on the CCN Family of Genes Nice, France 2015 (Abstract).
Brandan E et al. "Fibrosis Associated to Skeletal Muscle Devernation and to Amyotrophic Lateral Sclerosis (ALS) Model Role of CTGF/CCNN2" 8th International Workshop on the CCN Family of Genes Nice, France 2016 (Slide Presentation, Nov. 7, 2015).

* cited by examiner

*wild-type* hSOD1$^{G93A}$ + hIgG hSOD1$^{G93A}$ + FG-3019

*wild-type* hSOD1$^{G93A}$ + hIgG hSOD1$^{G93A}$ + FG-3019

METHODS FOR TREATMENT OF MOTOR NEURON DISEASES

FIELD OF THE INVENTION

The invention relates to methods and agents useful for treating motor neuron diseases (MNDs), in particular, amyotrophic lateral sclerosis (ALS). Methods and agents for treating various physiological and pathological features associated with motor neuron diseases are also provided.

BACKGROUND

Motor neuron diseases are a group of progressive, degenerative neurological disorders that destroy motor neurons, the cells that control essential voluntary muscle activity. As a result of motor neurons loss, the corresponding muscle fibers become denervated and atrophy (amyotrophy) leading to muscle weakness and in some diseases, muscle paralysis and death from respiratory failure.

In adults, the most common MND is amyotrophic lateral sclerosis (ALS), also known as Lou Gehrig's disease, that affects both upper (corticospinal neurons) and lower motor neurons (ventral horn of the spinal cord). ALS affects roughly 2 in 100,000 individuals each year with the disease more commonly seen in men than women (3:2 ratio). ALS typically manifests clinically in the fifth decade of life or later. As the disease progresses, patients require ventilatory assistance and ultimately die from respiratory failure about 2-3 years from clinical presentation.

Currently, the only approved therapy in the United States for MNDs is riluzole, 6-(trifluoromethoxy)benzothiazol-2-amine, approved for ALS. Riluzole is thought to act through the inhibition of glutamate release. Riluzole, unfortunately, only has modest effect, extending median survival by about 2 to 3 months.

In view of the devastating nature of the disease, and the lack of effective therapeutic approaches, a need exists for methods and agents useful for effectively treating MNDs, for reducing the rate of progression and severity of MNDs, and for preventing or reducing one or more symptoms of MNDs.

The invention meets this need by providing novel methods and agents for the treatment of MNDs by inhibiting connective tissue growth factor (CTGF) activity or expression.

SUMMARY OF THE INVENTION

In one aspect of the invention, a method is provided for treating a MND. The method comprises administering to a subject in need thereof, an effective amount of an anti-CTGF agent, thereby treating the MND. In some embodiments, the MND is selected from the group consisting of amyotrophic lateral sclerosis, primary lateral sclerosis, progressive muscular atrophy, spinal muscular atrophy, progressive bulbar palsy, pseudobulbar palsy, spinal-bulbar muscular atrophy, hereditary spastic paraplegia and post-polio syndrome. In particular embodiments, the MND is amyotrophic lateral sclerosis.

In another aspect of the invention, a method is provided for preventing or reducing a clinical symptom of a MND. The method comprises administering to a subject in need thereof an effective amount of an anti-CTGF agent, thereby preventing or reducing a clinical symptom of the MND. In some embodiments, the clinical symptom of the MND is selected from the group consisting of dysphagia, dysarthria, weight loss, muscle weakness, muscle fatigue, muscle spasticity, hyperreflexia and joint or muscle contractures, fasciculation or pain.

In another aspect, a method is provided for preventing the development of, or reducing the rate of progression of a MND. The method comprises administering to a subject in need thereof an effective amount of an anti-CTGF agent, thereby preventing the development of, or reducing the rate of progression of a MND.

In a further aspect, a method is provided for preventing or reducing muscle damage in a subject with muscular dystrophy, the method comprising administering to the subject a therapeutically effective amount of an anti-CTGF agent, thereby preventing or reducing muscle damage in the subject. In certain embodiments, the muscle damage is skeletal muscle damage.

These and other methods of the invention are accomplished by administering an anti-CTGF agent to the subject with a MND. In particular embodiments, the anti-CTGF agent is selected from the group consisting of anti-CTGF antibodies, anti-CTGF antibody fragments, antibody mimetics and anti-CTGF oligonucleotides. In some embodiments, the anti-CTGF agent is an anti-CTGF antibody. In further embodiments, the anti-CTGF antibody is a human or humanized antibody. In a specific embodiment, the anti-CTGF antibody is identical to CLN1 or mAb1 as described in U.S. Pat. No. 7,405,274. In further embodiments, the anti-CTGF antibody binds to domain 2 of human CTGF. In other embodiments, the anti-CTGF antibody binds to the same epitope as CLN1 or mAb1. In additional embodiments, the anti-CTGF oligonucleotide is selected from the group consisting of anti-CTGF antisense oligonucleotides, anti-CTGF siRNAs, anti-CTGF shRNAs, anti-CTGF miRNAs and anti-CTGF ribozymes. In certain embodiments, the anti-CTGF agent is used in combination with another therapeutic modality. In particular embodiments, the anti-CTGF agent is used in combination with an effective amount of riluzole.

These and other embodiments of the invention will readily occur to those of skill in the art in light of the disclosure herein, and all such embodiments are specifically contemplated. Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways.

BRIEF DESCRIPTION OF THE DRAWINGS

FIG. 6D shows the fraction of demyelinated axons present. About 1% of the total axons were demyelinated in wild-type mice compared to about 8% of the total axons in hSOD1$^{G93A}$ mice treated with huIgG. Treatment with FG-3019 significantly reduced the fraction of demyelinated axons in hSOD1$^{G93A}$ mice to about 6% of total axons. Data is mean±SEM and were derived from 3 fields per animal, n=3 for all groups. Significance was **p<0.01 and was calculated using one-way ANOVA. The results demonstrate that treatment with an anti-CTGF agent reduces demyelination of axons in a MND model.

FIGS. 7A-C show representative fields of neuromuscular junctions stained using antibodies against neurofilament-H, synaptic vesicle-2 (NF-H+SV2, green) and α-bungarotoxin (α-BTX, red). Arrows show innervated endplates and asterisks show denervated end-plates. Scale bar, 50 μm. FIG. 7D shows the percentage of innervated end-plates. Wild-type (n=1), hSOD1$^{G93A}$+huIgG (n=3) and hSOD1$^{G93A}$+FG-3019 (n=3). Three fields were examined per animal and data are shown as mean±SEM. These results demonstrate that treatment with an anti-CTGF agent reduces demyelination of axons in a MND model.

FIG. 9A illustrates the total distance traveled (m) in 10 minutes. Wild-type mice traveled approximately 4-fold further than hSOD1$^{G93A}$ mice treated with huIgG. Treatment with the anti-CTGF antibody FG-3019 increased the distance traveled by hSOD1$^{G93A}$ mice approximately 2-fold. FIG. 9B illustrates the average speed (m/s) of mice during the 10 minute test period. Wild-type mice traveled about 3.5-fold faster than hSOD1$^{G93A}$ mice treated with huIgG. Treatment with FG-3019 nearly doubled the average speed of hSOD1$^{G93A}$ mice compared to huIgG treated mice. N=3. These results demonstrate the ability of an anti-CTGF agent to preserve mobility (reduce the severity of muscle loss and control) in a MND model.

DESCRIPTION OF THE INVENTION

Figure 1:
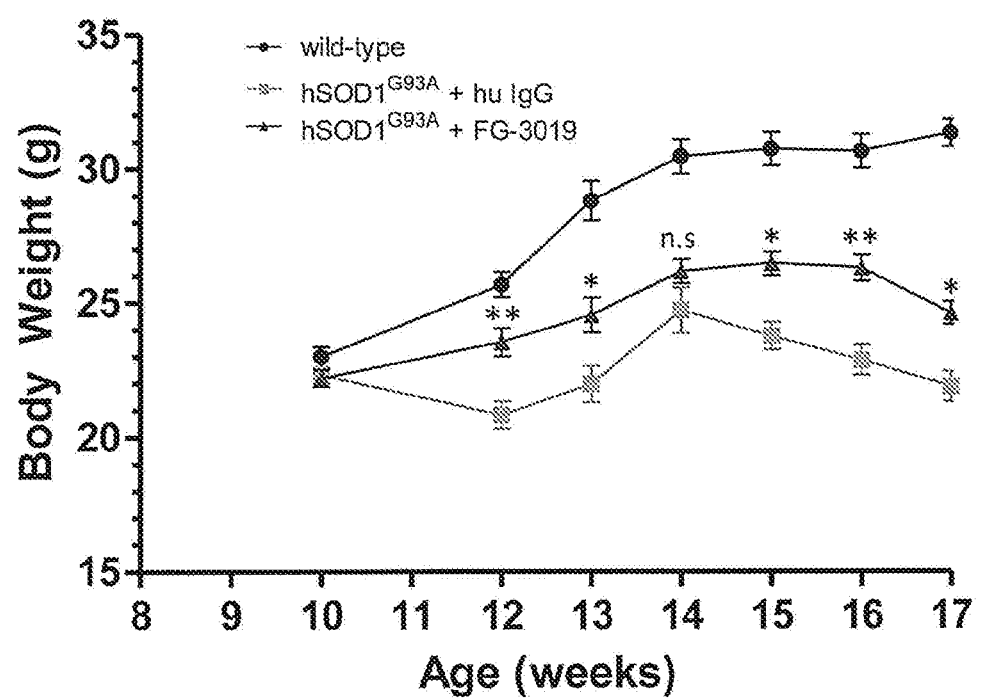
FIG. 1 illustrates the change in body weight over time for wild-type and hSOD1$^{G93A}$ mice. Over a seven week study period, wild-type mice steadily increased in body weight gaining about 30% in weight. In contrast, the body weight of hSOD1$^{G93A}$ mice treated with huIgG (25 mg/kg, i.p., 3 times per week) initially dropped, increased and then dropped again to end essentially unchanged at the end of the study period. Treatment of hSOD1$^{G93A}$ mice with the anti-CTGF antibody FG-3019 (25 mg/kg, 3 times per week) resulted in significantly higher body weight compared to hSOD1$^{G93A}$ mice treated with huIgG at all time points of the study except week 14. Two-way ANOVA, *p<0.05, **p<0.01. These results demonstrate that inhibition of CTGF reduces the extent of weight loss experienced in a MND model.

It is to be understood that the invention is not limited to the particular methodologies, protocols, cell lines, assays, and reagents described herein, as these may vary. It is also to be understood that the terminology used herein is intended to describe particular embodiments of the invention, and is in no way intended to limit the scope of the invention as set forth in the appended claims.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways.

It must be noted that as used herein and in the appended claims, the singular forms "a," "an," and "the" include plural references unless context clearly dictates otherwise. Thus, for example, a reference to "an anti-CTGF oligonucleotide" includes a plurality of such anti-CTGF oligonucleotides; a reference to "an antibody" is a reference to one or more antibodies and to equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the invention, the preferred methods, devices, and materials are now described. All publications cited herein are incorporated herein by reference in their entirety for the purpose of describing and disclosing the methodologies, reagents, and tools reported in the publications that might be used in connection with the invention. Nothing herein is to be construed as an admission that the invention is not entitled to antedate such disclosure by virtue of prior invention.

The practice of the invention will employ, unless otherwise indicated, conventional methods of chemistry, biochemistry, molecular biology, cell biology, genetics, immunology and pharmacology, within the skill of the art. Such techniques are explained fully in the literature. See, e.g., Gennaro, A R, ed. *Remington's Pharmaceutical Sciences*, 18th ed. Mack Publishing Co. (1990); Colowick, S et al., eds., *Methods In Enzymology*, Academic Press, Inc.; *Handbook of Experimental Immunology*, Vols. I-IV, D M Weir and C C Blackwell, eds., Blackwell Scientific Publications (1986); Maniatis, T. et al., eds. *Molecular Cloning: A Laboratory Manual*, 2nd edition, Vols. I-III, Cold Spring Harbor Laboratory Press (1989); Ausubel, F. M. et al., eds. *Short Protocols in Molecular Biology*, 4th edition, John Wiley & Sons (1999); Ream et al., eds. *Molecular Biology Techniques: An Intensive Laboratory Course*, Academic Press (1998); *PCR (Introduction to Biotechniques Series)*, 2nd ed. Newton & Graham eds., Springer Verlag (1997).

Definitions

As used herein, the term "about" refers to ±10% of the numerical value of the number with which it is being used. Therefore, the administration of about 15 mg/kg of an anti-CTGF antibody means the administration of 13.5 mg/kg-16.5 mg/kg of the antibody.

Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

As used herein, the term "subject," "individual," and "patient" are used interchangeably to refer to a mammal. In a preferred embodiment, the mammal is a primate, and more preferably a human being.

As used herein, the term "motor neuron diseases" or "MNDs" describes degenerative neurological disorders characterized by progressive loss of motor neurons of the brain ('upper motor neurons'), of the spinal cord ('lower motor neurons') or both, leading to atrophy and/or spasticity of the associated musculature. Motor neuron diseases include, for example, amyotrophic lateral sclerosis, primary lateral sclerosis (PLS), progressive muscular atrophy (PMA), spinal muscular atrophy (SMA), progressive bulbar palsy (PBP), pseudobulbar palsy, spinal-bulbar muscular atrophy (SBMA), hereditary spastic paraplegia (HSP) and post-polio syndrome. The traditional classification of MNDs is according to the affected cell types. PLS and pseudobulbar palsy affect upper motor neurons. PMA, PBP, SMA and SBMA affect lower motor neurons. Both upper and lower motor neurons are affected in ALS. The methods and agents of the invention may be used to treat any type of MND.

The terms "amyotrophic lateral sclerosis" and "ALS" as used herein refer to the group of neurodegenerative diseases characterized by the loss of motor neurons in the ventral horns of the spinal cord and the cortical neurons that provide their afferent input. ALS can initially affect principally either the upper or lower motor neurons, but irrespective of the primary lesion area, with time, the disease acquires a symmetrical generalized nature (Mitsumoto, H. et al. *Amyotrophic Lateral Sclerosis, In Contemporary Neurology Series* 49, Philadelphia, F. A. Davis Company (1998)). Both sporadic and familial forms of ALS occur with familial ALS, usually autosomal dominant, representing about 10% of ALS (Dion P A et al., *Nat. Rev. Genet.* 10:769-782 (2009)). ALS symptoms typically appear earlier in familial cases, but the clinical courses of familial and sporadic forms are comparable. Several types of genetic mutations have been identified as causative for the development of familial ALS with approximately 20% of the familial cases caused by inherited mutations in the protein Cu/Zn superoxide dismutase (SOD1) that protects motor neurons from free radical damage (Rosen D R et al., *Nature*, 362:59-62 (1993)).

Unlike some forms of familial ALS, the specific the etiology of sporadic ALS remains elusive with different hypotheses proposed including glutamate-mediated excitotoxicity, impaired mitochondrial function, oxidative stress, neuroinflammation and aberrant protein aggregation (Dib M, *Drugs*, 63: 289-310 (2003); Strong M J, *Pharmacology & Therapeutics*, 98:379-414 (2003); Bruijn L I et al., *Annu. Rev. Neurosci*, 27:723-749 (2004); Dibernardo A B et al., *Biochimica et Biophysica Acta*, 1762:1139-1149 (2006)).

The terms "primary lateral sclerosis" and "PLS," as used herein, refer to a progressive, degenerative disease of upper motor neurons characterized by progressive spasticity. PLS typically affects adults and is usually sporadic. It affects the lower extremities, trunk, upper extremities, and bulbar muscles, usually in that order. The major clinical challenge that the presentation of PLS poses is distinguishing it from ALS, hereditary spastic paraparesis and from nondegenerative conditions that may a similar presentation early in their course of development.

The terms "progressive muscular atrophy" and "PMA," as used herein, refer to an adult-onset, nonhereditary progressive neuromuscular disease clinically characterized by signs of lower motor neuron dysfunction and may evolve into ALS with upper motor neurons becoming affected.

The terms "spinal muscular atrophy" and "SMA," as used herein, refer to the leading genetic cause of infant death, affecting 1 in 10,000 live births per year (Pearn J, *J Med Genet* 15:414-417 (1978); Prior T W et al., *Am J Med Genet A*, 1; 152A(7):1608-1616 (2010)). Clinically, SMA is typified by progressive muscle weakness and loss of alpha motor neurons from the spinal cord. SMA is caused by mutations or deletions in the SMN1 gene (Lefebvre S et al., *Cell*, 80:155-165 (1995)). Due to a second, partially functionally copy, named SMN2, SMA is a disease of low SMN levels, rather than no SMN (Brzustowicz L M et al., *Hum Hered*, 43:380-387 (1993); Rochette C F et al., *Hum Genet*, 108: 255-266 (2001)). The clinical severity of SMA is categorized into 4 main types, which vary in their time of onset and expected prognosis. Furthermore, SMN2 serves as a disease modifier since the copy number of the SMN2 gene in SMA patients modulates disease severity.

The terms "progressive bulbar palsy" and "PBP," as used herein, refer to a neuromuscular disease that affects the lower motor neurons. Symptoms of PBP include pharyngeal muscle weakness that affect swallowing ability, jaw and facial muscle weakness, progressive loss of speech, and eventual atrophy of the tongue muscle. Limb weakness is almost always evident, but less prominent. Typically, PBP patients progress to ALS (Karam C et al. *Amyotroph Lateral Scler*, 11:364-368 (2010)).

As used herein, the term "pseudobulbar palsy" refers to a disease that shares many symptoms of PBP, but is characterized by degeneration of upper motor neurons. Affected individuals have progressive loss of the ability to speak, chew, and swallow. Progressive weakness in facial muscles leads to an expressionless face. Individuals may develop a gravelly voice and an increased gag reflex.

The terms "spinal-bulbar muscular atrophy," "SBMA" and "Kennedy's disease," as used herein, refer to an adult onset neuromuscular disease characterized by the degeneration and loss of lower motor neurons leading to muscle wasting. The disease affects an estimated 1-2 per 100,000 people. SBMA is characterized by late onset muscular atrophy beginning in the hips, then shoulders and progressing to muscles innervated by the brainstem (bulbar muscles), resulting in difficulty with walking, speech and swallowing (Atsuta N et al., *Brain,* 129:1446-1455 (2006); Fischbeck K H, *J Inherit Metab Dis,* 20:152-158 (1997); Kennedy W R et al., *Neurology,* 18:671-680 (1968)).

At the molecular level, SBMA is caused by the expansion of a polyglutamine (polyQ)-encoding CAG trinucleotide repeat in the first exon of the gene coding for the androgen receptor (AR). These repeats are toxic and lead to motor neuron death causing respiratory weakness in SBMA patients (Bricceno K V et al., *Neurodegener. Dis,* 9:199-209 (2012)). A correlation exists between the number of repeats and the age at onset of muscle weakness. Full disease manifestations are observed only in men while heterozygous females are mostly asymptomatic and women homozygous for the mutation are rare and show only mild symptoms (Schmidt B et al., *Neurology* 59:770-772 (2002)).

The terms "hereditary spastic paraplegia," "HSP" and "familial spastic paraparesis," as used herein, refer to a group of inherited disorders caused by corticospinal tract degeneration that manifests as progressive weakness and spasticity of the legs (Tallaksen C M et al. *Curr Opin Neurol,* 14:457-463 (2001)). The combined prevalence of all types of hereditary spastic paraplegias is estimated to be 1 to 10 in 100,000 people (Ruano L et al., *Neuroepidemlology,* 42:174-183 (2014)). Early clinical symptoms typically include mild gait difficulties and leg stiffness. These symptoms usually progress slowly and eventually lead to afflicted individuals requiring the assistance of a cane, walker, or wheelchair.

As used herein, the terms "post-polio syndrome" and "PPS" refer to neuromuscular disease that affects motor neurons that survived an initial acute infection with polo, a virus that infects and destroys motor neurons. About 25% to 65% of polio survivors develop PPS and post-polio muscular atrophy usually decades after their recovery from poliomyelitis when the surviving motor neurons are lost through aging, injury or disease (Ramlow J et al. *Am J Epidemiol,* 136:769-786 (1992); Windebank A J et al. *Neurology,* 41:501-507 (1991)). Symptoms include fatigue, slowly progressive muscle weakness, muscle atrophy, fasciculations, cold intolerance, and muscle and joint pain.

The terms, "treat," "treating" and "treatment," as used herein, refer to the administration of a therapeutic agent (e.g., anti-CTGF agent) to the subject in need thereof, in order to achieve a beneficial effect including preventing, stabilizing, reducing or reversing the development of a pathological condition of a cell type, tissue or organ affected by the MND; preventing, stabilizing, reducing or reversing one or more symptoms of a MND; improving the prognosis of the subject; or extending the survival of a subject with a MND. Treating a MND may increase the mobility of the subject, arrest the physical decline of the subject, reduce the need for medication or supportive measures, extend the period of independent living or freedom from the need for ventilator assistance or increase the time to needing a tracheostomy.

In some embodiments, the treated pathological condition affects neurons, including motor neurons, muscle cells, muscle fibers, Schwann cells, astrocytes, oligodendrocytes, microglia, T-cells and/or macrophages. In further embodiments, the pathological condition includes apoptosis, atrophy, axonal degradation, denervation, demyelination, fibrosis and inflammation, including neuroinflammation.

In further embodiments, treatment with an anti-CTGF agent prevents, stabilizes, reduces or reverses one or more symptoms of a MND including weight loss, muscle weakness, muscle fatigue, muscle cramps, muscle spasticity, muscle fasciculation, hyperreflexia, joint or muscle contractures, loss of control of voluntary muscle movement, difficulty breathing, dysphagia and dysarthria caused by muscle fiber (myofiber) atrophy and muscle fibrosis resulting from muscle denervation muscle. Additional MND symptoms that are prevented, stabilized, reduced or reversed by treatment with an anti-CTGF agent includes joint or muscle pain, emotional outbursts including uncontrollable periods of laughing or crying.

As used herein, the terms "reduce," "reducing" or "reduction" in the context of treating a subject with MND refers to treatment that eases, mitigates, alleviates, ameliorates or decreases the effect or severity of a pathological condition, or symptom of a MND, e.g., ALS, without curing the disease. Any indicia of success in reducing a pathological condition, or a symptom of a MND is recognized as reducing the pathological condition, or symptom. The reduction of a MND pathological condition, or symptom can be determined using standard routine clinical tests, observations and questionnaires that are well within the skill and knowledge of a medical professional. Non-limiting exemplary tests can include imaging tests, such as magnetic resonance imaging (MRI) or contrast myelography; neurophysiology tests, including electromyography tests, motor unit number estimation, electrical impedance myography, transcranial magnetic stimulation and nerve conduction velocity tests; observations made during a physical examination; as well as patient self-assessments and quality of life questionnaires.

In some embodiments, the methods of the invention reduce the occurrence or severity of a MND pathological condition, or symptom by at least 10%, at least 15%, at least 20%, at least 25%, at least 30%, at least 35%, at least 40%, at least 50%, at least 60%, at least 70%, at least 80% or at least 90% compared to a control group or historical controls.

When used in the context of the progression of a MND, the terms "reduce," "reducing" and "reduction" refer to slowing the rate of a pathological condition, a disease symptom or progression of the disease. In some embodiments, the methods of the invention slow the progression of a MND pathological condition or a MND symptom by at least 1 month, at least 2 months, at least 3 months, at least 4 months, at least 5 months, at least 6 months, at least 8 months, at least 10 months, at least 12 months, at least 15 months, at least 18 months or at least 24 months compared to a control group or a historical control. In additional embodiments, treatment of a subject with a MND with an anti-CTGF agent increases the survival of the subject MND by at least 10%, 20%, 30%, 40%, 50%, 60%, 70%, 80%, 90% or 100% compared to a control group or historical controls.

In other embodiments, the administration of an anti-CTGF agent increases survival of a subject with MND by at least 1 month, at least 2 months, at least 3 months, at least 4 months, at least 5 months, at least 6 months, at least 7 months, at least 8 months, at least 9 months, at least 10 months, at least 11 months, at least 12 months, at least 15 months, at least 18 months, at least 24 months at least 3 years, at least 4 years or at least 5 years compared to a control group or historical control.

As used herein, the term "effective amount"" in the context of administering an anti-CTGF agent to a subject with a MND or with a genetic susceptibility to develop a MND, refers to the amount of an anti-CTGF agent that is sufficient to produce a beneficial or therapeutic effect being sought by a researcher, veterinarian, physician, clinician or other healthcare practitioner including the prevention, stabilization, reduction or reversal in the severity of one or more pathological conditions of a cell, tissue or organ, or symptoms of the disease. In further embodiments, an "effective amount" of an anti-CTGF agent increases the survival of a subject with a MND.

In specific embodiments, an "effective amount" of an anti-CTGF agent refers to an amount of the anti-CTGF agent that is sufficient to prevent or delay the clinical presentation of at least one or more of the following symptoms in an individual with a MND or the genetic susceptibility to develop MND: weight loss, muscle weakness, muscle fatigue, muscle cramps, muscle spasticity, muscle fasciculation, hyperreflexia, joint or muscle contractures, loss of control of voluntary muscle movement, difficulty breathing, dysphagia, dysarthria, muscle or joint pain, emotional outbursts including uncontrollable periods of laughing or crying, or the development of pneumonia.

In other embodiments, an "effective amount" of an anti-CTGF agent refers to an amount of the anti-CTGF agent that is sufficient to stabilize (i.e., prevent the advancement) or slow the advancement of one or more MND symptoms; or reduce the severity of one or more symptoms of a MND including weight loss, muscle fatigue, muscle cramps, muscle spasticity, muscle fasciculation, hyperreflexia, joint or muscle contractures, loss of control of voluntary muscle movement, difficulty breathing, dysphagia, dysarthria, muscle or joint pain, emotional outbursts including uncontrollable periods of laughing or crying.

In further embodiments, an "effective amount" of an anti-CTGF agent refers to an amount of the anti-CTGF agent that is sufficient to prevent or reduce muscle damage, muscle wasting, muscle atrophy, muscle weakness, muscle degeneration, muscle fiber necrosis, muscle fibrosis, endomysial or perimysial inflammation and mononuclear inflammatory cell infiltration into muscle. In other embodiments, an "effective amount" of an anti-CTGF agent refers to an amount of the anti-CTGF agent that is sufficient to prevent or reduce demyelination of nerve fibers and axons, axonal degradation, or denervation of muscles.

Subjects

The present invention is based, in part, on the discovery of unexpected and surprising benefits to subjects with MNDs conferred through the inhibition of CTGF. Various methods and agents for treating MNDs are provided by the invention. Motor neuron disease refers to a group of muscle diseases characterized, in part, by progressive loss of motor neurons of the brain ('upper motor neurons'), spinal cord ('lower motor neurons') or both, leading to atrophy and/or spasticity of the associated musculature. In some embodiments, the subjects suitable for, or in need of treatment of the methods and anti-CTGF agents of the present invention are mammals, more preferably humans, who are at risk of developing a MND or have already displayed at least one symptom of a MND. Early symptoms of a MND often seen at the time of clinical presentation include problems in dexterity including asymmetric weakness of the hands that typically manifests as difficulty in picking up and holding objects and trouble performing fine motor tasks, shoulder weakness limiting arm movement above the head, trouble with gait and balance including increased tripping, and cramping and spasticity of the arms and legs. With bulbar-onset disease (e.g., PBP and pseudobulbar palsy) dysarthria is usually the first sign of the disease. Later appearing symptoms of a MND include dysphagia, dysarthria, muscle atrophy, muscle paralysis, muscle spasticity, hyperreflexia, fasciculations and joint or muscle contractures or pain.

Subjects suspected of having a MND can be readily identified by any competent medical practitioner using standard diagnostic tests and criteria including electrodiagnostic tests including electomyography (EMG) and nerve conduction velocity (NCV); blood and urine studies including high resolution serum protein electrophoresis; thyroid and parathyroid hormone levels; 24-hour urine collection for heavy metals; spinal tap; X-rays and magnetic resonance imaging (MRI) imaging studies; myelogram of cervical spine; neuromuscular ultrasound (NMUS); muscle and/or nerve biopsy; and a thorough neurological examination.

Diagnostic criteria for MNDs are well known in the art and include the revised El Escorial Criteria (Brooks B R et al. *Amyotroph Lateral Scler Other Motor Neuron Disord;* 1:293-299 (2000); EFNS Guidelines (Andersen P M et al. *Eur J Neurol,* 13:360-375 (2012)); and Awaji Criteria (Carvalho M, et al. *Shinkei Kenkyu No Shinpo,* 59:1023-1029 (2007)).

Genetic testing may also be employed to diagnose a subject with a MND. Techniques used in genetic testing include the polymerase chain reaction (PCR), Southern blotting, mutation scanning, and/or sequence analysis. DNA can be extracted from any relevant tissue or cell type including blood or white blood cells. The identification of subjects with a MND, including amyotrophic lateral sclerosis, or with a propensity to develop a MND, using genetic testing is specifically contemplated. Treatment of subjects with an anti-CTGF agent before the development of overt clinical symptoms of a MND may delay or prevent the development of clinical symptoms, thereby increasing the life span or quality of life of an affected individual.

Agents

In any of the methods described above, it is particularly contemplated that the agent or medicament that inhibits CTGF (i.e., the anti-CTGF agent or medicament) may be a polypeptide, polynucleotide, or small molecule; for example, an antibody that binds to CTGF, a CTGF antisense molecule, miRNA, ribozyme or siRNA, a small molecule chemical compound, etc. In some embodiments, inhibition of CTGF is accomplished using an antibody that specifically binds CTGF. In further embodiments, the invention contemplates inhibiting CTGF using an anti-CTGF oligonucleotide, but inhibition of CTGF can be accomplished by any of the means well-known in the art for modulating the expression or activity of CTGF.

Antibodies

The term "antibody" is used in the broadest sense and specifically covers monoclonal antibodies (including full length monoclonal antibodies), polyclonal antibodies, multispecific antibodies (e.g., bispecific antibodies), and antibody fragments, so long as they exhibit the desired biological activity. The term antibody further includes antibody mimetics, discussed further below.

The term "monoclonal antibody" as used herein refers to an antibody obtained from a population of substantially homogeneous antibodies, i.e., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations, which typically include different antibodies directed against different determinants (epitopes), each monoclonal antibody of a monoclonal antibody preparation is directed against a single determinant on an antigen.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler G and Milstein C, *Nature,* 256:495-497 (1975); Harlow E et al., *Antibodies: A Laboratory Manual* (Cold Spring Harbor Laboratory Press, 2nd ed. (1988); recombinant DNA methods (see, e.g., U.S. Pat. No. 4,816,567); phage-display technologies (see, e.g., Clackson T et al., *Nature,* 352: 624-628 (1991); Marks J D et al., *J Mol Biol* 222: 581-597 (1992); and Lee V et al., *J Immunol Methods* 284(1-2): 119-132 (2004)), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits A et al., *Proc Natl Acad Sci USA* 90: 2551 (1993); U.S. Pat. Nos. 5,545,807; 5,545,806; 5,569,825; 5,625,126; 5,633,425; and 5,661,016).

Monoclonal antibodies specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass (see, e.g., U.S. Pat. No. 4,816,567; and Morrison S et al., *Proc Natl Acad Sci USA* 81:6851-6855 (1984)).

"Humanized" forms of non-human (e.g., murine) antibodies are chimeric antibodies that contain minimal sequence derived from non-human immunoglobulin. In some embodiments, a humanized antibody is a human immunoglobulin (recipient antibody) in which residues from a one or more hypervariable regions (HVRs) of the recipient are replaced by residues from one or more HVRs of a non-human species (donor antibody) such as mouse, rat, rabbit, or nonhuman primate having the desired specificity, affinity, and/or capacity. For further details, see, e.g., Jones T A et al., *Nature* 321:522-525 (1986); Riechmann L et al., *Nature* 332:323-329 (1988); and U.S. Pat. Nos. 6,982,321 and 7,087,409.

A "human antibody" is one which possesses an amino acid sequence which corresponds to that of an antibody produced by a human and/or has been made using any of the techniques for making human antibodies (see e.g., Hoogenboom H R and Winter G, *J. Mol. Biol.,* 227:381 (1992); Marks J D et al., *J. Mol. Biol.,* 222:581 (1991); Boerner R et al., *J. Immunol.,* 147(1):86-95 (1991); Li J et al., *Proc. Natl. Acad. Sci. USA,* 103:3557-3562 (2006) and U.S. Pat. Nos. 6,075,181 and 6,150,584).

A "naked antibody" for the purposes herein is an antibody that is not conjugated to a cytotoxic moiety or a label, including a radiolabel. In some embodiments, the anti-CTGF antibody is a naked antibody.

The anti-CTGF antibodies of the invention may be specific for CTGF endogenous to the species of the subject to be treated or may be cross-reactive with CTGF from one or more other species. In some embodiments, the antibody for use in the present methods is obtained from the same species as the subject in need. In other embodiments, the antibody is a chimeric antibody wherein the constant domains are obtained from the same species as the subject in need and the variable domains are obtained from another species. For example, in treating a human subject the antibody for use in the present methods may be a chimeric antibody having constant domains that are human in origin and variable domains that are mouse in origin. In preferred embodiments, the antibody for use in the present methods binds specifically to the CTGF endogenous to the species of the subject in need. Thus, in certain embodiments, the antibody is a human or humanized antibody, particularly a monoclonal antibody, that specifically binds human CTGF (GenBank Accession No. NP_001892).

Exemplary antibodies for use in the treatment methods of the present invention are described, e.g., in U.S. Pat. No. 5,408,040; PCT/US1998/016423; PCT/US1999/029652 and International Publication No. WO 99/33878. Preferably, the anti-CTGF antibody is a monoclonal antibody. Preferably the antibody is a neutralizing antibody. In particular embodiments, the antibody is the antibody described and claimed in U.S. Pat. Nos. 7,405,274 and 7,871,617. In some embodiments, the antibody for treatment of a MND has the amino acid sequence of the antibody produced by the cell line identified by ATCC Accession No. PTA-6006. In other embodiments, the antibody binds to CTGF competitively with an antibody produced by ATCC Accession No. PTA-6006. In further embodiments, the antibody binds to the same epitope as the antibody produced by ATCC Accession No. PTA-6006. A particular antibody for use in the disclosed treatment methods is CLN1 or mAb1 as described in U.S. Pat. No. 7,405,274, or an antibody substantially equivalent thereto or derived therefrom. In some embodiments, the anti-CTGF antibody is CLN1, an antibody identical to the antibody produced by the cell line identified by ATCC Accession No. PTA-6006 that is encompassed by the claims of U.S. Pat. Nos. 7,405,274 and 7,871,617.

As referred to herein, the phrase "an antibody that specifically binds to CTGF" includes any antibody that binds to CTGF with high affinity. Affinity can be calculated from the following equation:

$$\text{Affinity} = K_a = \frac{[Ab \cdot Ag]}{[Ab][Ag]} = \frac{1}{K_d}$$

where [Ab] is the concentration of the free antigen binding site on the antibody, [Ag] is the concentration of the free antigen, [Ab·Ag] is the concentration of occupied antigen binding sites, $K_a$ is the association constant of the complex of antigen with antigen binding site, and $K_d$ is the dissociation constant of the complex. A high-affinity antibody typically has an affinity at least on the order of $10^8 \text{ M}^{-1}$, $10^9 \text{ M}^{-1}$ or $10^{10} \text{ M}^{-1}$. In particular embodiments, an antibody for use in the present methods will have a binding affinity for CTGF between of $10^8 \text{ M}^{-1}$ and $10^{10} \text{ M}^{-1}$, between $10^8 \text{ M}^{-1}$ and $10^9 \text{ M}^{-1}$ or between $10^9 \text{ M}^{-1}$ and $10^{10} \text{ M}^{-1}$. In some embodiments the high-affinity antibody has an affinity of about $10^8 \text{ M}^{-1}$, $10^9 \text{ M}^{-1}$ or $10^{10} \text{ M}^{-1}$.

"Antibody fragments" comprise a functional fragment or portion of an intact antibody, preferably comprising an antigen binding region thereof. A functional fragment of an antibody will be a fragment with similar (not necessarily identical) specificity and affinity to the antibody which it is derived. Non-limiting examples of antibody fragments include Fab, F(ab')$_2$, and Fv fragments that can be produced through enzymatic digestion of whole antibodies, e.g., digestion with papain, to produce Fab fragments. Other non-limiting examples include engineered antibody fragments such as diabodies (Holliger P et al. *Proc Natl Acad Sci USA*, 90: 6444-6448 (1993)); linear antibodies (Zapata G et al. *Protein Eng*, 8(10):1057-1062 (1995)); single-chain antibody molecules (Bird K D et al. *Science*, 242: 423-426 (1988)); single domain antibodies, also known as nanobodies (Ghahoudi M A et al. *FEBS Lett.* 414: 521-526, (1997)); domain antibodies (Ward E S et al. *Nature.* 341: 544-546, (1989)); and multispecific antibodies formed from antibody fragments.

Antibody Mimetics

Antibody mimetics are proteins, typically in the range of 3-25 kD, that are designed to bind an antigen with high specificity and affinity like an antibody, but are structurally unrelated to antibodies. Frequently, antibody mimetics are based on a structural motif or scaffold that can be found as a single or repeated domain from a larger biomolecule. Examples of domain-derived antibody mimetics include AdNectins that utilize the 10th fibronectin III domain (Lipovšek D. *Protein Eng Des Sel,* 24:3-9 (2010)); Affibodies that utilize the Z domain of staphylococcal protein A (Nord K et al. *Nat Biotechnol.* 15: 772-777 (1997)), and DARPins that utilize the consensus ankyrin repeat domain (Amstutz P. *Protein Eng Des Sel.* 19:219-229 (2006)). Alternatively, antibody mimetics can also be based on the entire structure of a smaller biomolecule, such as Anticalins that utilize the lipocalin structure (Beste G et al. *Proc Natl Acad Sci USA.* 5:1898-1903 (1999)). In some embodiments, the anti-CTGF antibody is an antibody mimetic.

Oligonucleotides

In some aspects, the present invention comprises synthetic oligonucleotides that decrease the expression of human CTGF mRNA. These anti-CTGF oligonucleotides include isolated nucleic acids, nucleic acid mimetics, and combinations thereof. Oligonucleotides of the invention comprise antisense oligonucleotides, ribozymes, external guide sequence (EGS) oligonucleotides (oligozymes) and inhibitory RNA (RNAi) including siRNA, microRNA (miRNA), and short hairpin RNA (shRNA). Oligonucleotides that decrease the expression of CTGF mRNA are useful for treating MNDs and in particular, ALS.

The terms "oligonucleotide" and "oligomeric nucleic acid" refer to oligomers or polymers of ribonucleic acid (RNA), deoxyribonucleic acid (DNA), mimetics or analogs of RNA or DNA, or combinations thereof, in either single- or double-stranded form. Oligonucleotides are molecules formed by the covalent linkage of two or more nucleotides or their analogs.

The terms "complementary" and "complementarity" refer to conventional Watson-Crick base-pairing of nucleic acids. For example, in DNA complementarity, guanine forms a base pair with cytosine and adenine forms a base pair with thymine, whereas in RNA complementarity, guanine forms a base pair with cytosine, but adenine forms a base pair with uracil in place of thymine. An oligonucleotide is complementary to a RNA or DNA sequence when the nucleotides of the oligonucleotide are capable of forming hydrogen bonds with a sufficient number of nucleotides in the corresponding RNA or DNA sequence to allow the oligonucleotide to hybridize with the RNA or DNA sequence. In some embodiments, the oligonucleotides have perfect complementarity to human CTGF mRNA, i.e., no mismatches.

When used in the context of an oligonucleotide, "modified" or "modification" refers to an oligonucleotide that incorporates one or more unnatural (modified) sugar, nucleobase or internucleoside linkage. Modified oligonucleotides are structurally distinguishable, but functionally interchangeable with naturally occurring or synthetic unmodified oligonucleotides and usually have enhanced properties such as increased resistance to degradation by exonucleases and endonucleases, or increased binding affinity. In some embodiments, the anti-CTGF oligonucleotides are modified.

Unnatural covalent internucleoside linkages, i.e., modified backbones, include those linkages that retain a phosphorus atom in the backbone and also those that do not have a phosphorus atom in the backbone. Numerous phosphorous containing modified oligonucleotide backbones are known in the art and include, for example, phosphoramidites, phosphorodiamidate morpholinos, phosphorothioates, phosphorodithioates, phosphotriesters, aminoalkylphosphotri-esters, methyl and other alkyl phosphonates including 3'-alkylene phosphonates, 5'-alkylene phosphonates and chiral phosphonates, and phosphinates. See Swayze E and Bhat B in *Antisense Drug Technology Principles. Strategies, and Applications.* 2nd Ed. CRC Press, Boca Rotan Fla., p. 144-182 (2008).

In further embodiments, the unnatural internucleoside linkages are uncharged and in others, the linkages are achiral. In some embodiments, the unnatural internucleoside linkages are uncharged and achiral, e.g., peptide nucleic acids (PNAs).

In some embodiments, the modified sugar moiety is a sugar other than ribose or deoxyribose. In certain embodiments, the sugar is arabinose, xylulose or hexose. In further embodiments, the sugar is substituted with one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C1 to C10 alkyl or C2 to C10 alkenyl and alkynyl. In some embodiments, the modifications include 2'-methoxy (2'-O—CH3), 2'-aminopropoxy (2'-OCH2CH2CH2NH2), 2'-allyl (2'-CH2-CH=CH2), 2'-O-allyl (2'-O—CH2-CH=CH2) and 2'-fluoro (2'-F). The 2'-modification may be in the arabino (up) position or ribo (down) position. Similar modifications may also be made at other positions on an oligonucleotide, particularly the 3' position of the sugar on the 3' terminal nucleotide or in 2'-5' linked oligonucleotides and the 5' position of 5' terminal nucleotide.

In some embodiments, the modified sugar is conformationally restricted. In further embodiments, the conformational restriction is the result of the sugar possessing a bicyclic moiety. In other embodiments, the bicyclic moiety links the 2'-oxygen and the 3' or 4'-carbon atoms. In additional embodiments the linkage is a methylene (—CH2-)n group bridging the 2' oxygen atom and the 4' carbon atom, wherein n is 1 or 2. This type of structural arrangement produces what are known as "locked nucleic acids" (LNAs). See Koshkin A A et al. *Tetrahedron,* 54, 3607-3630 (1998); and Singh S K et al., *Chem. Commun,* 4:455-456 (1998).

In some embodiments, the sugar is a sugar mimetic that is conformationally restricted resulting in a conformationally constrained monomer. In certain embodiments, the sugar mimetic comprises a cyclohexyl ring that comprises one ring heteroatom and a bridge making the ring system bicyclic. See PCT/US2010/044549. In further embodiments, the oligonucleotides comprise at least one nucleotide that has a bicyclic sugar moiety or is otherwise conformationally restricted.

In some embodiments, the modified sugar moiety is a sugar mimetic that comprises a morpholino ring. In further embodiments, the phosphodiester internucleoside linkage is replaced with an uncharged phosphorodiamidate linkage. See Summerton J and Weller D, *Antisense Nucleic Acid Drug Dev,* 7: 187-195 (1997).

In some embodiments, both the phosphate groups and the sugar moieties are replaced with a polyamide backbone comprised of repeating N-(2-aminoethyl)-glycine units to which the nucleobases are attached via methylene carbonyl linkers. These constructs are called peptide nucleic acids (PNAs). PNAs are achiral, uncharged and because of the peptide bonds, resistant to endo- and exonucleases. See Nielsen P E et al., *Science,* 254:1497-1500 (1991) and U.S. Pat. No. 5,539,082.

Oligonucleotides useful in the methods of the invention include those comprising entirely or partially of naturally occurring nucleobases. Naturally occurring nucleobases include adenine, guanine, thymine, cytosine, uracil, 5-methylcytidine, pseudouridine, dihydrouridine, inosine, ribothymidine, 7-methylguanosine, hypoxanthine and xanthine.

Oligonucleotides further include those comprising entirely or partially of modified nucleobases (semi-synthetically or synthetically derived). See Herdewijn P, *Antisense Nucleic Acid Drug Dev* 10: 297-310 (2000); and Sanghvi Y S, et al. *Nucleic Acids Res,* 21: 3197-3203 (1993).

In some embodiments, at least one nucleoside, i.e., a joined base and sugar, in an oligonucleotide is modified, i.e., a nucleoside mimetic. In certain embodiments, the modified nucleoside comprises a tetrahydropyran nucleoside, wherein a substituted tetrahydropyran ring replaces the naturally occurring pentofuranose ring. See PCT/US2010/022759 and PCT/US2010/023397. In other embodiments, the nucleoside mimetic comprises a 5'-substituent and a 2'-substituent. See PCT/US2009/061913. In some embodiments, the nucleoside mimetic is a substituted α-L-bicyclic nucleoside. See PCT/US2009/058013. In additional embodiments, the nucleoside mimetic comprises a bicyclic sugar moiety. See PCT/US2009/039557. In further embodiments, the nucleoside mimetic comprises a bis modified bicyclic nucleoside. See PCT/US2009/066863. In certain embodiments, the nucleoside mimetic comprises a bicyclic cyclohexyl ring wherein one of the ring carbons is replaced with a heteroatom. See PCT/US2009/033373. In still further embodiments, a 3' or 5'-terminal bicyclic nucleoside is attached covalently by a neutral internucleoside linkage to the oligonucleotide. See PCT/US2009/039438. In other embodiments, the nucleoside mimetic is a tricyclic nucleoside. See PCT/US2009/037686.

The oligonucleotides of the invention can contain any number of the modifications described herein. The aforementioned modifications may be incorporated uniformly across an entire oligonucleotide, at specific regions or discrete locations within the oligonucleotide including at a single nucleotide. Incorporating these modifications can create chimeric or hybrid oligonucleotides wherein two or more chemically distinct areas exist, each made up of one or more nucleotides.

Oligonucleotides of the invention can be synthesized by any method known in the art, e.g., using enzymatic synthesis and/or chemical synthesis. The oligonucleotides can be synthesized in vitro (e.g., using enzymatic synthesis and chemical synthesis) or in vivo (using recombinant DNA technology well known in the art). In a preferred embodiment, chemical synthesis is used for modified polynucleotides. Chemical synthesis of linear oligonucleotides is well known in the art and can be achieved by solution or solid phase techniques. Preferably, synthesis is by solid phase methods. Automated, solid phase oligonucleotide synthesizers used to construct the oligonucleotides of the invention are available through various vendors including GE Healthcare Biosciences (Piscataway, N.J.).

Oligonucleotide synthesis protocols are well known in the art and can be found, e.g., in U.S. Pat. No. 5,830,653; WO 98/13526; Stec W et al. *J Am Chem Soc* 106:6077-6079 (1984); Stec W et al. *J Org. Chem* 50:3908-3913 (1985); Stec W et al. *J Chromatog* 326:263-280 (1985); LaPlanche J L et al. *Nucl Acid Res* 26:251-60 (1986); Fasman G D, *Practical Handbook of Biochemistry and Molecular Biology* (1989). CRC Press, Boca Raton, Fla.; U.S. Pat. No. 5,013,830; U.S. Pat. No. 5,214,135; U.S. Pat. No. 5,525,719; WO 92/03568; U.S. Pat. No. 5,276,019; and U.S. Pat. No. 5,264,423.

As used herein, the term "antisense oligonucleotide" refers to an oligomeric nucleic acid that is capable of hybridizing with its complementary target nucleic acid sequence resulting in the impairment of the normal function of the target nucleic acid sequence. Antisense oligonucleotides that inhibit CTGF expression have been described and utilized to decrease CTGF expression in various cell types. (See, e.g., PCT/US1996/008140; PCT/US1999/026189; PCT/US1999/029652; PCT/US2002/038618; Kothapalli D et al. *Cell Growth Differ* 8:61-68, 1997; Shimo T et al. *J Biochem* (Tokyo) 124:130-140 (1998); Uchio K et al. *Wound Repair Regen* 12:60-66 (2004); Guha M et al. *FASEB J* 21:3355-3368 (2007); U.S. Pat. No. 6,358,741; U.S. Pat. No. 6,965,025; U.S. Pat. No. 7,462,602; U.S. Patent Application Publication No. 2008/0070856; U.S. Patent Application Publication No. 2008/0176964; and U.S. Pat. No. 8,802,839; PCT/US02/38618; PCT/US2009/054973; PCT/US2009/054974; PCT/US2009/054975; PCT/US2009/054976; PCT/US2012/023620; and U.S. patent application Ser. No. 13/364,547, incorporated herein by reference in their entirety.

In some embodiments, the oligonucleotides used to decrease the expression of human CTGF mRNA are small interfering RNA (siRNA). As used herein, the terms "small interfering RNA" or "siRNA" refer to single- or double-stranded RNA molecules that induce the RNA interference (RNAi) pathway and act in concert with host proteins, e.g., RNA induced silencing complex (RISC) to degrade mRNA in a sequence-specific fashion. In naturally occurring RNAi, a double-stranded RNA (dsRNA) is cleaved by the RNase III/helicase protein, Dicer, into small interfering RNA (siRNA) molecules. These siRNAs are incorporated into a multicomponent-ribonuclease called RNA-induced silencing complex (RISC). One strand of siRNA remains associated with RISC and guides the complex toward a cognate RNA that has sequence complementary to the guider ss-siRNA in RISC. This siRNA-directed endonuclease digests the RNA, thereby inactivating it.

Selective silencing of CTGF expression by RNAi can be achieved by administering isolated siRNA oligonucleotides or by the in vivo expression of engineered RNA precursors (see U.S. Pat. Nos. 7,056,704, 7,078,196, 7,459,547, 7,691,995 and 7,691,997).

In some embodiments, treatment methods are provided wherein patients are administered a recombinant expression vector that expresses anti-CTGF oligonucleotides. Such genetic constructs can be designed using appropriate vectors and expressional regulators for cell- or tissue-specific expression and constitutive or inducible expression. These genetic constructs can be formulated and administered according to established procedures within the art. In some embodiments, patients are administered recombinant expression vectors that encode a short hairpin oligonucleotide. In further embodiments, the recombinant expression vectors are DNA plasmids, while in other embodiments, the expression vectors are viral vectors. RNA expressing viral vectors can be constructed based on, but not limited to, adeno-associated viruses, retroviruses, adenoviruses, or alphaviruses. In some embodiments, the expression vectors persist in target cells. Alternatively, such vectors can be repeatedly administered as necessary.

In some embodiments, the decrease in expression of CTGF mRNA by an anti-CTGF oligonucleotide comprises the interference in the function of the target CTGF DNA sequence (CTGF gene), typically resulting in decreased replication and/or transcription of the target CTGF DNA. In other embodiments, the decrease in expression of CTGF mRNA by an anti-CTGF oligonucleotide comprises the interference in function of CTGF RNA, typically resulting in impaired splicing of transcribed CTGF RNA (pre-mRNA) to yield mature mRNA species, decreased CTGF RNA stability, decreased translocation of the CTGF mRNA to the site of protein translation and impaired translation of protein from mature mRNA. In other embodiments, the decrease in expression of CTGF mRNA by an anti-CTGF oligonucleotide comprises the decrease in cellular CTGF mRNA number or cellular content of CTGF mRNA. In some embodiments, the decrease in expression of CTGF mRNA by an anti-CTGF oligonucleotide comprises the down-regulation or knockdown of CTGF gene expression. In other embodiments, the decrease in expression of CTGF mRNA by an anti-CTGF oligonucleotide comprises the decrease in CTGF protein expression or cellular CTGF protein content.

In some embodiments, the methods of the invention comprise the administration of an effective amount of an anti-CTGF oligonucleotide that decreases CTGF mRNA transcription rate, cellular CTGF mRNA level, CTGF expression rate, cellular CTGF protein level or interstitial CTGF protein level. In further embodiments, the methods of the invention comprise the administration of an effective amount of an anti-CTGF oligonucleotide that decreases CTGF mRNA transcription rate, cellular CTGF mRNA level, CTGF expression rate, cellular CTGF protein level by at least 5%, at least 10%, at least 15%, at least 20%, at least 25%, at least 30%, at least 35%, at least 40%, at least 45%, at least 50%, at least 60%, at least 70%, at least 80% or at least 90% compared to controls.

Administration and Dosage

An effective amount of an anti-CTGF agent or pharmaceutical composition thereof can be administered as often as necessary, e.g., once, twice or three times per day, every other day, once, twice or three times per week, every other week, every three weeks or monthly. The skilled artisan will appreciate that certain factors may influence the dosage and timing required to effectively treat a subject, including but not limited to the severity or extent of the disease, the administration route, previous treatments, concurrent medications, performance status, weight, gender, race or ethnicity, and/or age of the subject. In certain embodiments, the methods for treating a MND presented herein comprise the administration to a subject in need thereof an anti-CTGF agent at a range from about 0.01 mg to about 10,000 mg, from about 0.1 mg to about 5,000 mg, from about 1.0 mg to about 2,500 mg, from about 1.0 mg to about 1,000 mg, from about 10 mg to about 500 mg, from about 100 mg to about 1,000 mg, from about 0.10 mg to about 50 mg or from about 0.5 mg to about 50 mg.

In some embodiments, the methods for treating a MND presented herein comprise the administration to a subject in need thereof at least about 0.1 mg, 0.5 mg, 1.0 mg, 2.0 mg, 4 mg, 8 mg, 16 mg, 25 mg, 50 mg, 100 mg, 200 mg, 400 mg, 800 mg, 1,000 mg, 2,000 mg, 3,000 mg, 5,000 mg or 10,000 mg of an anti-CTGF agent. In some embodiments, the methods for treating a MND presented herein comprise the administration to a subject in need thereof not more than about 1 mg, 5 mg, 10 mg, 20 mg, 30 mg, 40 mg, 50 mg, 60 mg, 70 mg, 80 mg, 90 mg, 100 mg, 150 mg, 175 mg, 200 mg, 250 mg, 500 mg, 750 mg, 1,000, 2,000, 5,000 mg or 10,000 mg of an anti-CTGF agent.

In further embodiments, the methods for treating a MND presented herein comprise the administration to a subject in need thereof an anti-CTGF agent from about 0.001 mg/kg to about 5,000 mg/kg, about 0.01 mg/kg to about 1000 mg/kg, about 0.1 mg/kg to about 500 mg/kg or about 1.0 mg/kg to about 100 mg/kg.

In some embodiments, an effective amount of an anti-CTGF antibody is administered at a dose of between about 1 mg/kg to 100 mg/kg, 5 mg/kg to 75 mg/kg, 10 mg/kg to 50 mg/kg, 15 mg/kg to 45 mg/kg or 20 mg/kg to 45 mg/kg. In other embodiments, an effective amount of the anti-CTGF antibody comprises a dose of about 15 mg/kg, 20 mg/kg, 25 mg/kg, 30 mg/kg, 35 mg/kg, 40 mg/kg, 45 mg/kg or 50 mg/kg. In further embodiments, the anti-CTGF antibody is administered systemically, e.g., i.v. administration.

In further embodiments, treatment with an anti-CTGF antibody comprises the administration of an initial loading dose. As used herein, the term "loading dose" refers to an initial antibody dose used to rapidly achieve a desired antibody target level, typically, a target steady-state antibody level or an antibody level that correlates with a desired pharmacological or clinical response. A loading dose can be administered as a single injection or infusion, or alternatively, the loading dose can be administered as multiple antibody injections or infusion within an initial treatment time frame, e.g., three infusions of 15 mg/kg spaced over 21 days of a 28 day treatment cycle for a total infusion of 45 mg/kg. In particular embodiments, the loading dose is at least 15 mg/kg, 20 mg/kg, 22.5 mg/kg, 25 mg/kg, 30 mg/kg, 35 mg/kg, 40 mg/kg, 45 mg/kg, 50 mg/kg, 55 mg/kg, 60 mg/kg, 70 mg/kg, 80 mg/kg, 100 mg/kg or 120 mg/kg. In specific embodiments, the loading dose is about 15 mg/kg, 20 mg/kg, 25 mg/kg, 30 mg/kg, 35 mg/kg, 45 mg/kg, 55 mg/kg or 60 mg/kg.

In some embodiments, an effective amount of an anti-CTGF oligonucleotide comprises a dose between about 0.01 mg to about 1,000 mg, about 0.1 mg to about 100 mg, about 1.0 mg to about 50 mg, about 1.0 mg to about 25 mg, or about 5 mg to about 50 mg.

In further embodiments, the methods for treating a MND presented herein comprise the administration to a subject in need thereof of an anti-CTGF agent or a pharmaceutical composition thereof at a dosage that achieves a target plasma, or tissue concentration of the anti-CTGF agent. In particular embodiments, the administered dosage achieves a plasma or tissue concentration of the anti-CTGF agent ranging from about 0.001 µg/mL to about 100 mg/mL, about 0.01 µg/mL to about 10 mg/mL, about 0.1 µg/mL to about 1 mg/mL or about 1 µg/mL to about 100 µg/ml in a subject with a MND. In other embodiments, the administration to a subject in need thereof of an anti-CTGF antibody achieves a plasma or tissue target concentration of the anti-CTGF antibody of at least about 10 µg/ml, at least about 50 µg/ml, at least about 100 µg/mL, at least about 200 µg/mL, at least about 300 µg/mL or at least about 400 µg/mL. In further embodiments, the administration to a subject in need thereof of an anti-CTGF antibody achieves a plasma or tissue target concentration of a range of about 1.0 µg/ml to about 2,000 µg/ml, about 10 µg/mL to about 1,000 µg/mL, or about 20 µg/mL to about 500 µg/mL.

In certain embodiments, subsequent doses of an anti-CTGF agent may be adjusted accordingly based on the plasma or tissue concentration of the anti-CTGF agent achieved with earlier doses of the anti-CTGF agent. In general, the dosage and frequency of administration of an anti-CTGF agent may be adjusted over time to provide sufficient levels of the anti-CTGF agent to maintain the desired effect.

Combination Therapy

In some embodiments, the methods for treating a MND, e.g., ALS, provided herein involve the administration of an anti-CTGF agent in combination with one or more additional therapies. As used herein, the term "in combination" refers to the administration of the anti-CTGF agent prior to, concurrent with, or subsequent to the administration of one or more additional therapies for use in treating a MND or a symptom of a MND. The use of the term "in combination" does not restrict the order in which the anti-CTGF agent and the one or more additional therapies are administered to a subject. The additional therapies may be administered by the same route or a different route of administration than used for the anti-CTGF agent.

In some embodiments, the additional therapy administered in combination with the anti-CTGF agent is a drug or pharmaceutical composition comprising a drug. In particular embodiments, the anti-CTGF agent is administered in combination with riluzole. In other embodiments, the anti-CTGF agent is administered in combination with an effective amount of one or more drugs selected from the group consisting of amitriptyline; andrographolide; anticonvulsants; antispasmodics (e.g., tizanidine, oxybutynin chloride); arimoclomol; atropine; AVP-923; basiliximab; benzodiazepines (e.g., diazepam, clonazepam); ceftriaxone; celecoxib; cistanche total glycosides; CK-2017357; coenzyme Q10; copper; corticotropin; creatine; deferiprone; dexpramipexole; dronabinol; escitalopram; ezogabine; fasudil; fingolimod; glatiramer acetate; glycopyrrolate; GM604; granulocyte colony stimulating factor, growth hormone (somatropin); GSK1223249; imipranmine; incobotulinum toxin A; inosine; insulin like growth factor type 1; interleukin 1 receptor antagonist; interleukin-2 (IL-2); involuntary muscle relaxants (e.g., tolterodine tartate); ISIS 333611; KNS-760704; levetiracetam; lithium carbonate; MCI-186; mecobalamin; memantine; methylprednisolone; mexiletine; minocycline; MN-166; mycophenolate mofetil; nonsteroidal anti-inflammatory drugs (NSAIDs); nortriptyline; NP001; ODM-109; olanzapine; ONO-2506PO; opiates; ozanezumab; pimozide; pioglitazone; R(+) pramipexole; prednisone; propantheline; pyrimethamine; rasagiline; riluzole; RNS60; SB-509; scopolamine; l-serine; sNN0029; sodium phenylbutyrate; sodium valproate; tacrolimus; talampanel; tamoxifen; tauroursodeoxycholic acid; TCH346; thalidomide; tirasemtiv; tocilizumab; tretinoin; TRO19622; voluntary muscle relaxants (e.g., baclofen); YAM80; and zinc.

In further embodiments, the anti-CTGF agent is administered in combination with another therapy including far infrared radiation; phenique nerve stimulation; transplantation of stem or progenitor cells including spinal cord derived neural stem cells, mesioangioblasts, adipocyte stem cells, autologous bone marrow stem cells, bone marrow mesenchymal stem cells or stromal cells, bone marrow mobilized CD133+ hematopoietic stem cell and CD34+ progenitor cells from peripheral blood or umbilical cord blood and induced pluripotent stem cells; dietary supplementation, e.g., Oxepa, Jevity 1.5, Jevity 1.0, KetoCal or Calogen; gene therapy, e.g., VM202; exercise; ventilatory assistance (e.g., intermittent positive pressure ventilation, bilevel positive airway pressure, biphasic cuirass ventilation); occupational therapy; and physical therapy.

In specific embodiments, the interval of time between the administration of an anti-CTGF agent and the administration of one or more additional therapies may be about 0 to 15 minutes, 0 to 30 minutes, 30 minutes to 60 minutes, 1 to 2 hours, 2 to 6 hours, 2 to 12 hours, 12 to 24 hours, 1 to 2 days, 2 to 4 days, 4 to 7 days, 1 to 2 weeks, 2 to 4 weeks, 4 to 12 weeks, 12 to 24 weeks, or 24 to 52 weeks. In certain embodiments, an anti-CTGF agent and one or more additional therapies are administered less than 1 day, 1 week, 2 weeks, 3 weeks, 4 weeks, one month, 2 months, 3 months, 6 months, or 1 year apart.

In some embodiments, the administration of an anti-CTGF agent in combination with one or more additional therapies has an additive effect, while in other embodiments the combination of therapies has a synergistic effect. In specific embodiments, a synergistic effect achieved with combination therapy permits the use of lower dosages (e.g., sub-optimal conventional doses) of the additional therapy, e.g., riluzole. In other embodiments, the synergistic effect achieved with combination therapy allows for a less frequent administration of the additional therapy to a subject. In certain embodiments, the ability to utilize lower dosages of an additional therapy and/or to administer the additional therapy less frequently reduces the toxicity associated with the administration of the additional therapy, without reducing the efficacy of the additional therapy. In some embodiments, a synergistic effect results in improved efficacy of an anti-CTGF antibody and/or the additional therapies in treating a MND.

The combination of an anti-CTGF agent and one or more additional therapies can be administered to a subject in the same pharmaceutical composition. Alternatively, an anti-CTGF agent and one or more additional therapies can be administered concurrently to a subject in separate pharmaceutical compositions. An anti-CTGF agent and one or more additional therapies may also be administered to a subject by the same or different routes of administration.

Pharmaceutical Formulations and Routes of Administration

The compositions and compounds suitable for use in the methods of the present invention can be delivered directly or in pharmaceutical compositions containing excipients, as is well known in the art. Various formulations and drug delivery systems are available in the art and depend in part on the intended route of administration. (See, e.g., Gennaro A R, ed. *Remington's Pharmaceutical Sciences*, (2000); and Hardman J G, Limbird L E, and Gilman L S, eds. *The Pharmacological Basis of Therapeutics*, (2001))

Suitable routes of administration may, for example, include oral, rectal, topical, nasal, pulmonary, intestinal, and parenteral administration. Primary routes for parenteral administration include intravenous, intramuscular, and subcutaneous administration. Secondary routes of administration include intraperitoneal and intra-arterial administration.

Pharmaceutical dosage forms of a suitable compound for use in the invention may be provided in an instant release, controlled release, sustained release, or target drug-delivery system. Commonly used dosage forms include, for example, solutions and suspensions, (micro-) emulsions, ointments, gels and patches, liposomes, tablets, dragees, soft or hard shell capsules, suppositories, ovules, implants, amorphous or crystalline powders, aerosols, and lyophilized formulations. Depending on route of administration used, special devices may be required for application or administration of the drug, such as, for example, syringes and needles, inhalers, pumps, injection pens, applicators, or special flasks. Pharmaceutical dosage forms are often composed of the drug, an excipient(s), and a container/closure system. One or multiple excipients, also referred to as inactive ingredients, can be added to a compound of the invention to improve or facilitate manufacturing, stability, administration, and safety of the drug, and can provide a means to achieve a desired drug release profile. Therefore, the type of excipient(s) to be added to the drug can depend on various factors, such as, for example, the physical and chemical properties of the drug, the route of administration, and the manufacturing procedure. Pharmaceutically acceptable excipients are available in the art, and include those listed in various pharmacopoeias. (See, e.g., USP, JP, EP, and BP), Inactive Ingredient Guide available through the FDA's website, and *Handbook of Pharmaceutical Additives*, ed. Ash; Synapse Information Resources, Inc. (2002))

Pharmaceutical dosage forms of a compound for use in the present invention may be manufactured by any of the methods well-known in the art, such as, for example, by conventional mixing, sieving, dissolving, melting, granulating, dragee-making, tabletting, suspending, extruding, spray-drying, levigating, emulsifying, (nano/micro-) encapsulating, entrapping, or lyophilization processes. As noted above, the compositions for use in the present invention can include one or more physiologically acceptable inactive ingredients that facilitate processing of active molecules into preparations for pharmaceutical use.

Proper formulation is dependent upon the desired route of administration. For intravenous injection, for example, the composition may be formulated in aqueous solution, if necessary, using physiologically compatible buffers, including, for example, phosphate, histidine, or citrate for adjustment of the formulation pH, and a tonicity agent, such as, for example, sodium chloride or dextrose. For transmucosal or nasal administration, semisolid, liquid formulations, or patches may be preferred, possibly containing penetration enhancers. Such penetrants are generally known in the art.

For oral administration, the compounds can be formulated in liquid or solid dosage forms and as instant or controlled/sustained release formulations. Suitable dosage forms for oral ingestion by a subject include tablets, pills, dragees, hard and soft shell capsules, liquids, gels, syrups, slurries, suspensions, and emulsions.

Solid oral dosage forms can be obtained using excipients, which may include, fillers, disintegrants, binders (dry and wet), dissolution retardants, lubricants, glidants, antiadherants, cationic exchange resins, wetting agents, antioxidants, preservatives, coloring, and flavoring agents. These excipients can be of synthetic or natural source. Examples of such excipients include cellulose derivatives, citric acid, dicalcium phosphate, gelatine, magnesium carbonate, magnesium/sodium lauryl sulfate, mannitol, polyethylene glycol, polyvinyl pyrrolidone, silicates, silicium dioxide, sodium benzoate, sorbitol, starches, stearic acid or a salt thereof, sugars (i.e. dextrose, sucrose, lactose, etc.), talc, tragacanth mucilage, vegetable oils (hydrogenated), and waxes. Ethanol and water may serve as granulation aides. In certain instances, coating of tablets with, for example, a taste-masking film, a stomach acid resistant film, or a release-retarding film is desirable. Natural and synthetic polymers, in combination with colorants, sugars, and organic solvents or water, are often used to coat tablets, resulting in dragees. When a capsule is preferred over a tablet, the drug powder, suspension, or solution thereof can be delivered in a compatible hard or soft shell capsule.

Compositions formulated for parenteral administration by injection are usually sterile and, can be presented in unit dosage forms, e.g., in ampoules, syringes, injection pens, or in multi-dose containers, the latter usually containing a preservative. The compositions may take such forms as suspensions, solutions, or emulsions in oily or aqueous vehicles, and may contain formulatory agents, such as buffers, tonicity agents, viscosity enhancing agents, surfactants, suspending and dispersing agents, antioxidants, biocompatible polymers, chelating agents, and preservatives. Depending on the injection site, the vehicle may contain water, a synthetic or vegetable oil, and/or organic co-solvents. In certain instances, such as with a lyophilized product or a concentrate, the parenteral formulation would be reconstituted or diluted prior to administration. Depot formulations, providing controlled or sustained release of a compound of the invention, may include injectable suspensions of nano/micro particles or nano/micro or non-micronized crystals. Polymers such as poly(lactic acid), poly(glycolic acid), or copolymers thereof, can serve as controlled/sustained release matrices, in addition to others well known in the art. Other depot delivery systems may be presented in form of implants and pumps requiring incision.

Suitable carriers for intravenous injection for the molecules of the invention are well-known in the art and include water-based solutions containing a base, such as, for example, sodium hydroxide, to form an ionized compound, sucrose or sodium chloride as a tonicity agent, for example, the buffer contains phosphate or histidine. Co-solvents, such as, for example, polyethylene glycols, may be added. These water-based systems are effective at dissolving compounds of the invention and produce low toxicity upon systemic administration. The proportions of the components of a solution system may be varied considerably, without destroying solubility and toxicity characteristics. Furthermore, the identity of the components may be varied. For example, low-toxicity surfactants, such as polysorbates or poloxamers, may be used, as can polyethylene glycol or other co-solvents, biocompatible polymers such as polyvinyl pyrrolidone may be added, and other sugars and polyols may substitute for dextrose.

Anti-CTGF antibody formulations for use in accordance with the present invention may be prepared by mixing an anti-CTGF antibody with pharmaceutically acceptable carriers, excipients or stabilizers that are nontoxic to recipients at the dosages and concentrations employed. Anti-CTGF antibody formulations may include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); carriers; hydrophilic polymers such as polyvinylpyrrolidone; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes; and/or non-ionic surfactants or polyethylene glycol.

In particular, anti-CTGF antibody formulations may further comprise low molecular weight polypeptides; carriers such as serum albumin, gelatin, or immunoglobulins; and amino acids such as glycine, glutamine, asparagine, histidine, arginine, or lysine. The anti-CTGF antibody formulations can be lyophilized as described in PCT/US1996/012251. Additionally, sustained-release preparations may also be prepared. Frequently, polymers such as poly(lactic acid), poly(glycolic acid), or copolymers thereof serve as controlled/sustained release matrices, in addition to others well known in the art.

The anti-CTGF antibodies can be supplied or administered at any desired concentration. In some embodiments, the anti-CTGF antibody concentration is at least 1 mg/ml, 5 mg/ml, 10 mg/ml, 20 mg/ml, 25 mg/ml, 50 mg/ml, 75 mg/ml, 100 mg/ml, 125 mg/ml, 150 mg/ml, or 200 mg/ml. In other embodiments, the anti-CTGF antibody concentration is no more than about 5 mg/ml, 10 mg/ml, 20 mg/ml, 25 mg/ml, 50 mg/ml, 75 mg/ml, 100 mg/ml, 125 mg/ml, 150 mg/ml, 200 mg/ml, 250 mg/ml, or 300 mg/ml. In further embodiments, the anti-CTGF antibody concentration is between 5 mg/ml to 20 mg/ml, 20 mg/ml to 50 mg/ml, 50 mg/ml to 100 mg/ml, 100 mg/ml to 200 mg/ml, or 200 mg/ml to 300 mg/ml.

Articles of Manufacture

The present compositions may, if desired, be presented in a pack or dispenser device containing one or more unit dosage forms containing an anti-CTGF agent. Such a pack or device may, for example, comprise metal or plastic foil, glass and rubber stoppers, vials or syringes. The container holding an anti-CTGF agent composition that is effective for treating a MND and may have a sterile access port (for example the container may be an intravenous solution bag or a vial having a stopper pierceable by a hypodermic injection needle). The article of manufacture may further comprise an additional container comprising a pharmaceutically acceptable diluent buffer, such as bacteriostatic water for injection (BWFI), phosphate-buffered saline, Ringer's solution, and/or dextrose solution. The article of manufacture may further include other materials desirable from a commercial and user standpoint, including, for example, filters or needles.

Compositions comprising an anti-CTGF agent formulated in a compatible pharmaceutical carrier may be provided in an appropriate container that is labeled for treatment of a MND. The pack or dispenser device may be accompanied by instructions for administration that provide specific guidance regarding dosing the anti-CTGF agent including a description of the type of patients who may be treated (e.g., a person with ALS), the schedule (e.g., dose and frequency) and route of administration, and the like.

These and other embodiments of the present invention will readily occur to those of ordinary skill in the art in view of the disclosure herein.

EXAMPLES

The invention will be further understood by reference to the following examples, which are intended to be purely exemplary of the invention. These examples are provided solely to illustrate the claimed invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description and accompanying figures. Such modifications are intended to fall within the scope of the appended claims.

The most widely used transgenic mouse strain to model ALS is the SOD1 mouse, which expresses a human SOD1 transgene with a causative glycine-to-alanine change at residue 93 (G93A mutation) (Gurney M E, et al., *Science* 264:1772-1775 (1994)). This mouse model has an onset of hind limb weakness at about 90 days, accompanied by degenerative changes to motor neurons that compare well with human ALS pathology (Synofzik M et al., *J Neurol Neurosurg Psychiatry* 81:764-767 (2010)). The transgenic mice additionally fail to gain weight compared to wild-type mice. Morbidity develops around ~120 days and death by about ~125-127 days, depending on genetic background.

Example 1: CTGF Inhibition Ameliorates Weight Loss in an Animal Model of ALS

To study the effects of CTGF inhibition on an animal model of ALS, male 8-week-old hSOD1$^{G93A}$ mice were administered intraperitoneally either non-specific human IgG (huIgG, FibroGen, Inc., San Francisco, Calif.) or a fully human monoclonal IgG antibody that specifically binds CTGF (FG-3019, FibroGen, Inc.). The antibodies were administered at 25 mg/Kg, three times per week for 2 months. B6.SJL (wild-type) mice served as control. Mice were weighted weekly starting at age 10 weeks (FIG. 1).

Over the seven week study period, wild-type mice increased in body weight by 36.5%. In contrast, the body weight of hSOD1$^{G93A}$ mice treated with huIgG was essentially unchanged at −2.8% by the end of the study period. Surprisingly, treatment of hSOD1$^{G93A}$ mice with FG-3019 caused a significant increase in body weight with the FG-3019 treated mice exhibiting an 11.3% increase in body weight compared to huIgG treated hSOD1$^{G93A}$ mice at the end of the study. This experiment demonstrates the ability of an anti-CTGF agent to ameliorate a clinical symptom of ALS, weight loss associated with ALS progression.

Example 2: CTGF Inhibition Reduces Fibronectin Expression

Mice in Example 1 were sacrificed at the conclusion of the 2 month treatment period and samples of gastrocnemius and tibialis anterior muscles were harvested (Morales M G et al.

Hum. Mol. Genet. 22:4938-4951 (2013)). To test the ability of FG-3019 to reduce the production of extracellular matrix (ECM) components and hence, the development of muscle fibrosis, the presence of fibronectin was analyzed by immunoblot analysis. Additionally, the samples were examined for Smad3 and GAPDH expression. Briefly, muscles were homogenized in 10 volumes of Tris-EDTA buffer with 1 mM phenylmethylsulfonyl fluoride (PMSF). Total protein concentration was determined for aliquots of muscle extracts using a bicinchoninic acid protein assay kit (TheroFisher Scientific, Waltham, Mass.), with bovine serum albumin (BSA) as the standard. Aliquots (60 µg) were subjected to sodium dodecyl sulfate (SDS) gel electrophoresis in 9% polyacrylamide gels, electrophoretically transferred onto PVDF membranes (Schleicher & Schuell Bioscience, Inc., Keene, N.H.) and sequentially probed with specific antibodies against CTGF (Santa Cruz Biotechnology, Santa Cruz, Calif., USA), fibronectin (Sigma-Aldrich, St. Louis, Mo.), collagen III (Rockland, USA), total Smad-3 (Cell Signaling Technologies, Danvers, Mass.) and GAPDH (EMD Millipore, Billerica, Mass.). All immunoreactions were visualized by enhanced chemiluminescence (ThermoFisher Scientific). Densitometric analysis and quantification were performed using the ImageJ software (National Institutes of Health, Bethesda, Md.).

Figure 2A:
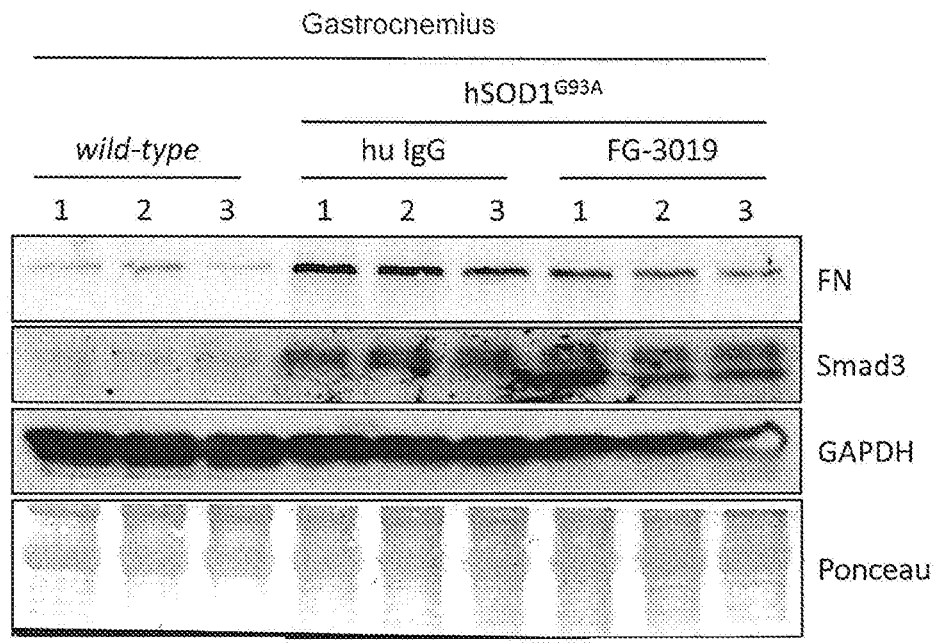
FIGS. 2A-C show a Western blot of protein extracts from gastrocnemius muscle (FIG. 2A) and normalized protein expression results (FIGS. 2B and 2C). The blot was probed sequentially for fibronectin (FN), mothers against decapentaplegic homolog 3 (Smad3) and glyceraldehyde 3-phosphate dehydrogenase (GAPDH). Protein bands were visualized with Ponceau S stain. Wild-type mice exhibited minimal fibronectin expression (FIGS. 2A and 2B). In contrast, fibronectin expression was moderately increased in hSOD1$^{G93A}$ mice treated with huIgG. Treatment with the anti-CTGF antibody FG-3019 significantly reduced the level of fibronectin expression in hSOD1$^{G93A}$ mice, p<0.005, n=6. Wild-type mice exhibited low levels of Smad3 (FIGS. 2A and 2C). On the other hand, Smad3 expression was markedly elevated in hSOD1$^{G93A}$ mice treated with huIgG. Treatment with FG-3019 did not significantly reduce the expression of Smad3 compared wild-type mice. These results demonstrate that inhibition of CTGF reduces fibronectin expression.
Figure 2B:
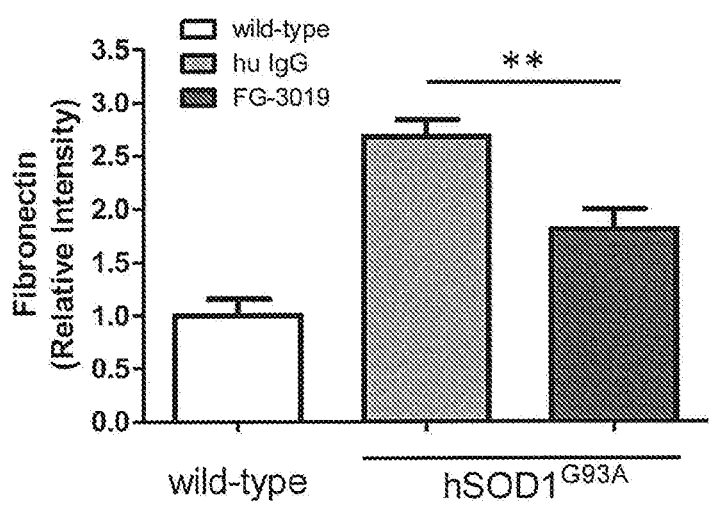

Muscle samples from wild-type mice exhibit minimal fibronectin expression, FIGS. 2A and 2B. In contrast, the level of fibronectin (FN) was approximately 2.7-fold higher in hSOD1$^{G93A}$ mice treated with huIgG compared to wild-type mice. Treatment with FG-3019 significantly reduced the level of fibronectin in hSOD1$^{G93A}$ mice muscle tissue to about 1.8-fold higher over that seen in wild-type mice, $p<0.005$, $n=6$.

Figure 2C:
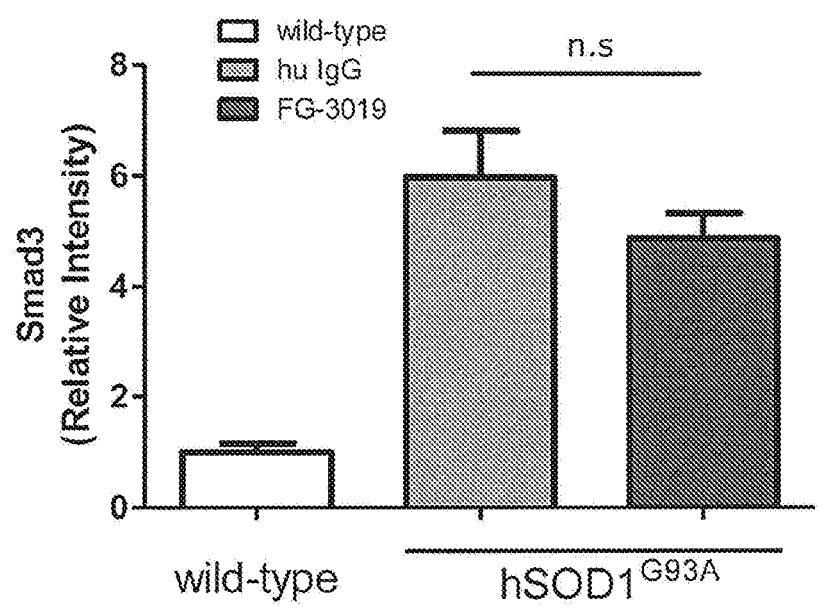

Wild-type mice exhibited nominal expression of Smad3, a mediator of the TGF-β signaling pathway. FIGS. 2A and 2C. On the other hand, Smad3 expression was markedly elevated in hSOD1$^{G93A}$ mice treated with huIgG, approximately 6-fold higher than control. Smad3 expression in hSOD1$^{G93A}$ mice treated with FG-3019 was approximately 4.9-fold higher than control. The difference in Smad3 expression between huIgG and FG-3019 treated hSOD1$^{G93A}$ mice was not statistically significant.

These results demonstrate that inhibition of CTGF activity reduces the expression of the ECM constituent, fibronectin, in skeletal muscle obtained from an animal model of ALS. Increased expression of ECM occurs during the development of skeletal muscle fibrosis as damaged and necrotic muscle is replaced by ECM. These results demonstrate that the agents and methods of the invention are effective at reducing ECM deposition and hence, muscle fibrosis in a model of ALS. The reduction in this pathological condition seen in muscle tissue from a model of ALS suggests that anti-CTGF agents would be effective for treating ALS and other MNDs.

Example 3: CTGF Inhibition Reduces EMC Deposition

Samples of gastrocnemius muscle were obtained from mice in Example 1 at the end of the treatment period and snap-frozen in isopentane. Cryosectioned samples (7 mm) were fixed in 4% paraformaldehyde, blocked for 1 h in 5% BSA in PBS and incubated for 1 hour at room temperature with specific antibodies against fibronectin (Sigma-Aldrich), collagen-I (EMD Millipore), laminin (Sigma-Aldrich) and phospho-Smad3 (Cell Signaling Technologies). As the secondary antibody, Alexa-conjugated goat anti-rabbit IgG and rabbit anti-mouse IgG (ThermoFisher Scientific) were used. For monoclonal anti-mouse antibodies, all the incubations were performed with mouse IgG-blocking solution from a mouse on mouse kit (Vector Laboratories, Burlingame, Calif.) diluted in 0.01% Triton X-100/PBS. For nuclear staining, the sections were incubated with 1 mg/ml Hoechst 33258 in PBS for 10 min. For total collagen staining, the sections were incubated in 1% Sirius Red in picric acid. After rinsing, the coverslips were mounted and viewed an inverted microscope equipped for epifluorescence.

Analysis of slides demonstrated that FG-3019 treated hSOD1$^{G93A}$ mice had reduced fibronectin, collagen-1 and total collagen deposition compared to the huIgG treated hSOD1$^{G93A}$ mice. These results show that inhibition of CTGF activity reduces ECM deposition and hence, reduces muscle fibrosis in an ALS model. The reduction in muscle fibrosis suggests that anti-CTGF agents would be effective for treating ALS and other MNDs.

Example 4: CTGF Inhibition Reduces Muscle Atrophy

Histology slides of gastrocnemius muscle prepared in Example 3 that were stained with an anti-laminin antibody and Hoechst 33258 were analyzed to determine the Feret's diameter of individual muscle fibers. Five randomly captured images were analyzed using Image J software. Individual muscle fibers were manually selected and the minimal Feret's diameter of each fiber was computed by the software (Morales M G et al. 2013, supra).

Figure 3:
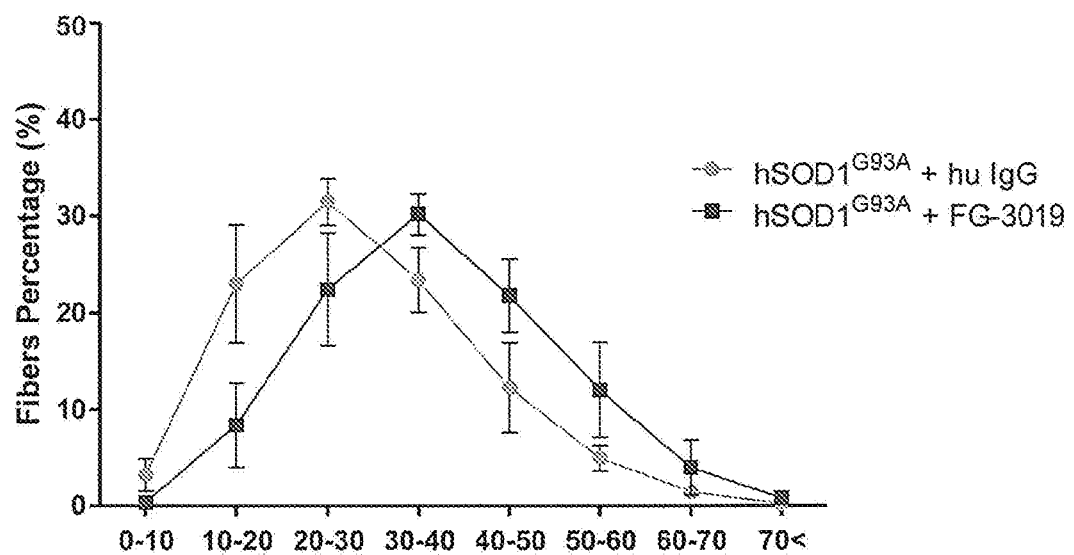
FIG. 3 illustrates the size distribution of Feret's diameter (μm) of gastrocnemius muscle fibers from hSOD1$^{G93A}$ mice treated with huIgG or FG-3019. hSOD1$^{G93A}$ mice treated with huIgG had, in general, muscle fibers with smaller Feret's diameter compared to hSOD1$^{G93A}$ mice treated with FG-3019. These results demonstrate that inhibition of CTGF reduces muscle atrophy in a MND model.

Muscle fibers from FG-3019 treated hSOD1$^{G93A}$ mice had larger Feret's diameters than huIgG treated hSOD1$^{G93A}$ mice (FIG. 3). The results demonstrate that inhibition of CTGF reduces the development of muscle atrophy as evidenced by the prevalence of larger diameter muscle fibers in the FG-3019 treated hSOD1$^{G93A}$ mice. These results suggest that FG-3019 treated hSOD1$^{G93A}$ mice will have increased muscle strength compared to huIgG treated hSOD1$^{G93A}$ mice. Further, the results suggest that treatment with an anti-CTGF agent will preserve muscle strength or reduce the rate at which strength is lost by a subject afflicted with ALS or other MNDs.

Example 5: CTGF Inhibition Preserves Muscle Strength

Samples of diaphragm, gastrocnemius and tibialis anterior muscles were obtained from mice in Example 1 at the end of the treatment period. The isometric force of isolated muscles was measured as described previously (Morales M G et al. (2013); Acuña M J, et al. Hum Mol Genet 23(5): 1237-1249 (2014); Cabrera D et al. Skelet. Muscle 4(6) (2014)). Briefly, the optimum muscle length (Lo) and stimulation voltage were determined from the micromanipulation of muscle length to produce a maximum isometric twitch force. Maximum isometric tetanic force (Po) was determined from the plateau of the frequency-force relationship after successive stimulations at 1-200 Hz for 450 ms, with 2 min rests between the stimuli. After measuring the isometric contractile properties, muscles were subjected to a tetanic stimulation protocol that was performed three times. Muscles at Lo were maximally stimulated for 450 ms once every 5 s. After functional testing, muscles were removed from the bath, trimmed of their tendons and any adhering non-muscle tissue, blotted once on a filter paper and weighed. Muscle mass and Lo were used to calculate the specific net force (force normalized per total muscle fiber cross-sectional area, mN/mm$^2$).

Figure 4A:
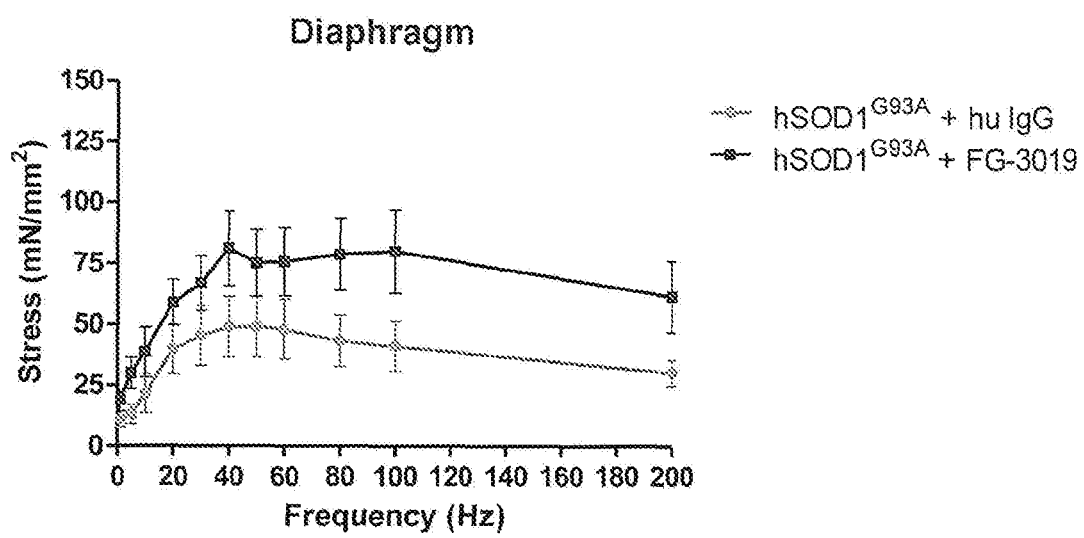
FIGS. 4A and 4B illustrate, respectively, the isometric force generated by diaphragm and tibialis anterior muscles from hSOD1$^{G93A}$ mice. Muscles from hSOD1$^{G93A}$ mice treated with huIgG generated about half the isometric force across all frequencies tested compared to muscles from hSOD1$^{G93A}$ mice treated with FG-3019. These results demonstrate that treatment with an anti-CTGF antibody preserves muscle strength in a MND model.
Figure 4B:
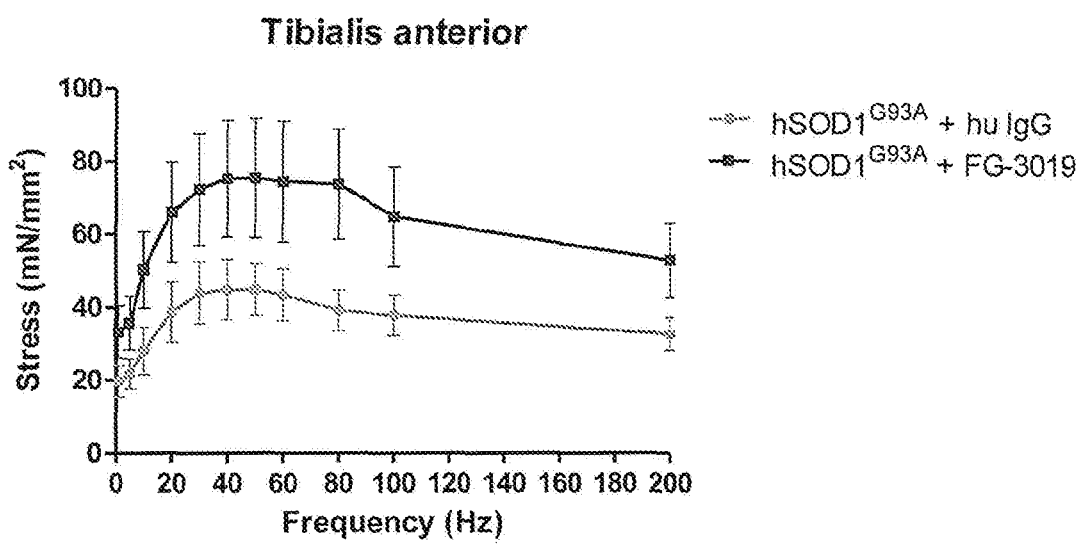

Compared with skeletal muscle from wild-type mice (not shown), skeletal muscle obtained from hSOD1$^{G93A}$ mice administered huIgG showed a reduction in maximum isometric tetanic force. This reduction in muscle function was expected and mirrors what is seen in human subjects with ALS and other MNDs. Treatment with FG-3019 increased the maximum isometric tetanic force of muscle from hSOD1$^{G93A}$ mice (FIGS. 4A and 4B). These results indicate that muscle weakness is reduced by inhibition of CTGF in an animal model of ALS. These results further suggest that the use of an anti-CTGF agent would provide an effective treatment for ALS and other MNDs.

Figure 5A:
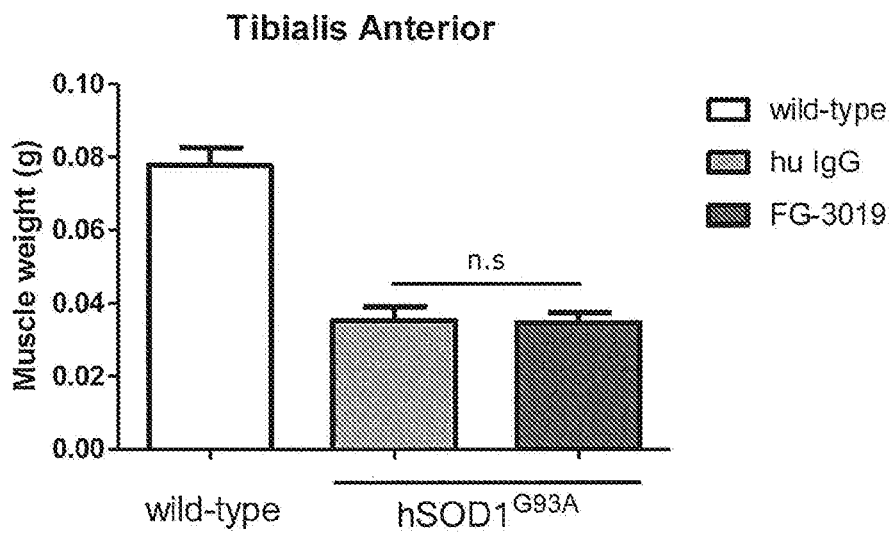
FIGS. 5A and 5B illustrate, respectively, the weight of tibialis anterior and gastrocnemius muscle from wild-type and hSOD1$^{G93A}$ mice treated with huIgG or FG-3019. The muscles of wild-type mice were about twice as heavy as the muscles from either group of hSOD1$^{G93A}$ mice. Treatment with an anti-CTGF agent did not appear to significantly influence muscle weight in a MND model.
Figure 5B:
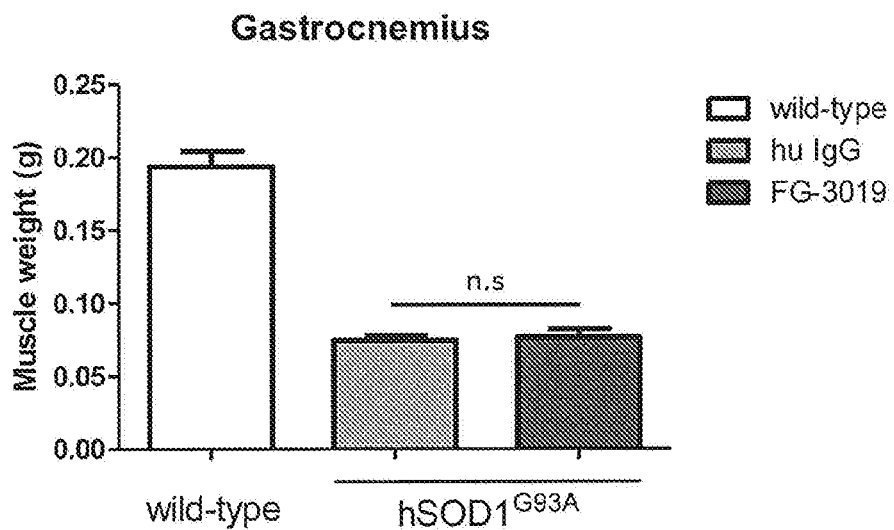

Interestingly, muscle weights obtained from hSOD1$^{G93A}$ mice treated with huIgG or FG-3019 were not significantly different (FIGS. 5A and 5B).

Example 6: CTGF Inhibition Reduces Nerve Demyelination

Figure 6A:
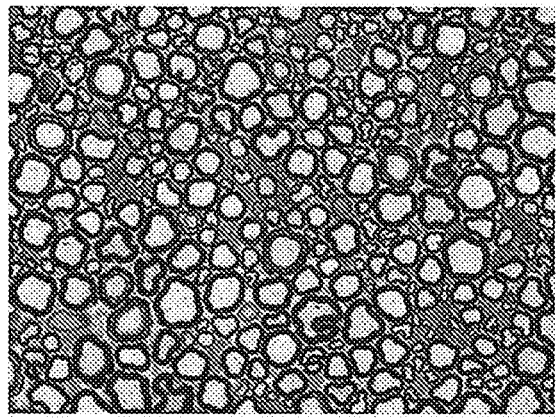
FIGS. 6A-D illustrate the degree of sciatic nerve demyelination present in toluidine stained sections from wild-type mice and hSOD1$^{G93A}$ mice treated with huIgG or FG-3019. Representative images of sectioned nerves are shown in FIGS. 6A-C. Images are 100× and the scale bar is 10 nm. White asterisks show demyelinated axons.
Figure 6B:
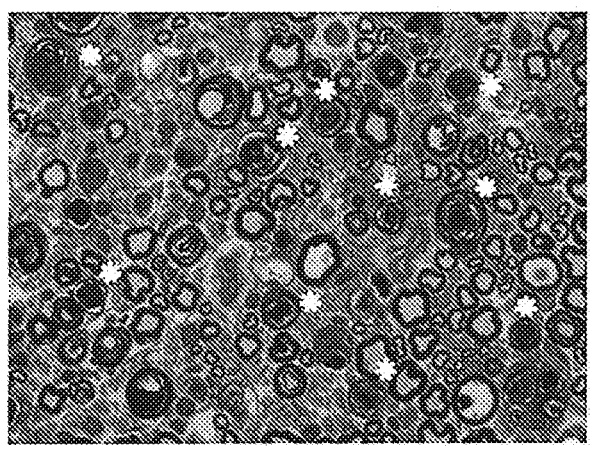
Figure 6C:
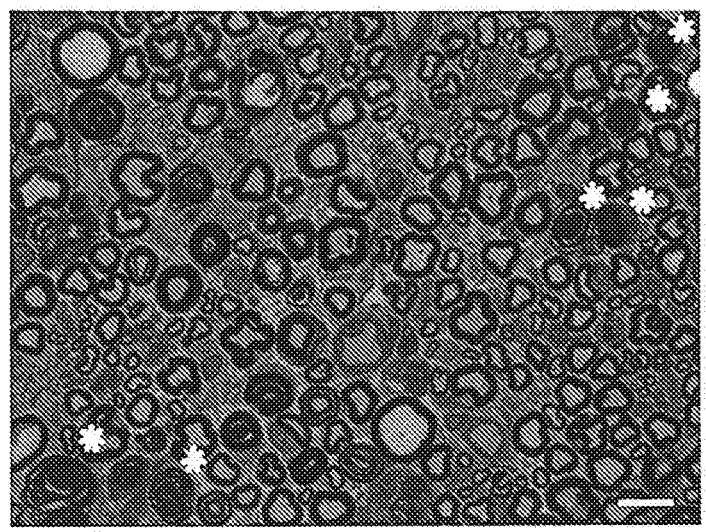
Figure 6D:
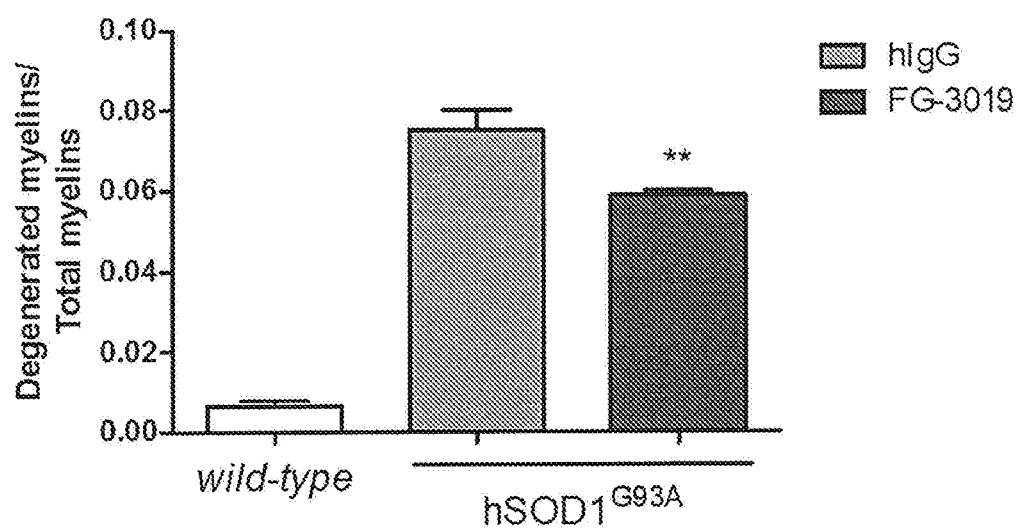

Simples of sciatic nerves were obtained from the mice in Example 1 at the end of the treatment period. Sections were stained with toluidine blue and then examined microscopically to ascertain the fraction of axons that were demyelinated. Representative images are shown in FIGS. 6A-C. Images are 100× and the scale bar is 10 μm. White asterisks show demyelinated axons. FIG. 6D shows the fraction of axons that are demyelinated. About 0.01 of the total axons were demyelinated in wild-type mice compared to about 0.08 of the total axons in hSOD1$^{G93A}$ mice treated with huIgG. Treatment with FG-3019 significantly reduced the fraction of demyelinated axons in hSOD1$^{G93A}$ mice to about 0.06 of total axons. Data is mean±SEM and were derived from 3 fields per animal, n=3 for all groups. Significance was **p<0.01 and was calculated using one-way ANOVA. The results demonstrate that treatment with an anti-CTGF agent reduces demyelination of axons in an ALS model. As demyelination is linked to loss of axons and denervation of muscles, the results suggest that treatment with an anti-CTGF agent will reduce denervation of muscles, thereby reducing muscle atrophy, muscle damage and muscle fibrosis in subjects with ALS and other MNDs.

Example 6: CTGF Inhibition Reduces Muscle Denervation

Figure 7A:
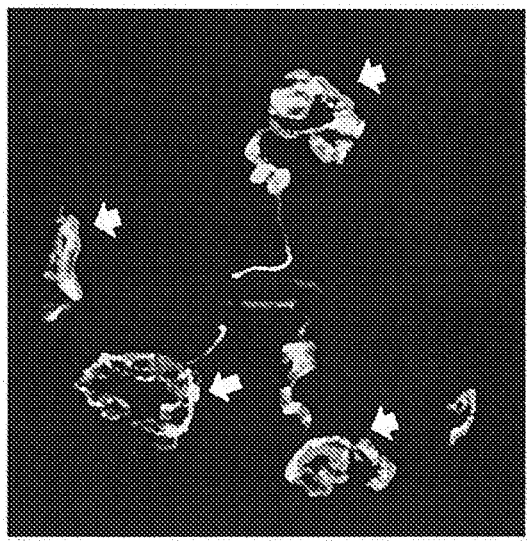
FIGS. 7A-D illustrate the degree of innervation of diaphragm neuromuscular junctions in wild-type and hSOD1$^{G93A}$ mice.
Figure 7B:
Figure 7C:
Figure 7D:
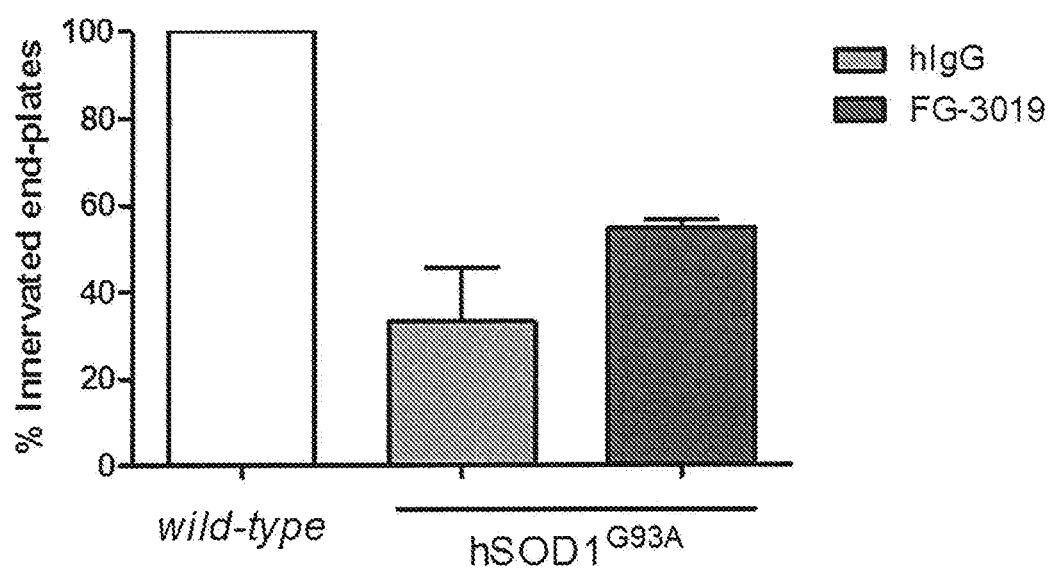

Diaphragm muscle samples were obtained from the mice in Example 1 at the end of the treatment period. The muscle samples were sectioned and then stained with antibodies against neurofilament-H (Sigma Aldrich), synaptic vesicle-2, (Development Studies Hybridoma Bank, University of Iowa) and α-bungarotoxin (Invitrogen, Waltham, Mass.). The diaphragm neuromuscular junctions were examined to ascertain the degree of innervation with three fields examined per animal, wild-type, n=1; hSOD1$^{G93A}$ mice treated with huIgG, n=3; and hSOD1$^{G93A}$ treated with FG-3019, n=3. FIGS. 7A-C shows representative fields of neuromuscular junctions with arrows showing innervated end-plates and asterisks showing denervated end-plates. Scale bar, 50 μm. FIG. 7D shows the percentage of innervated end-plates for each group. Wild-type (n=1), hSOD1$^{G93A}$+huIgG (n=3) and hSOD1$^{G93A}$+FG-3019 (n=3). Three fields were examined per animal and data are shown as mean±SEM. These results demonstrate that treatment with an anti-CTGF agent reduces muscle denervation in an ALS model. As muscle denervation is causally related the development of muscle atrophy, muscle damage, the deposition of ECM matrix constituents and the development of muscle fibrosis, the results further suggest that treatment with an anti-CTGF agent may reduce the development of these pathological conditions seen in ALS and other MNDs.

Example 7: CTGF Inhibition Delays Disease Progression

Figure 8:
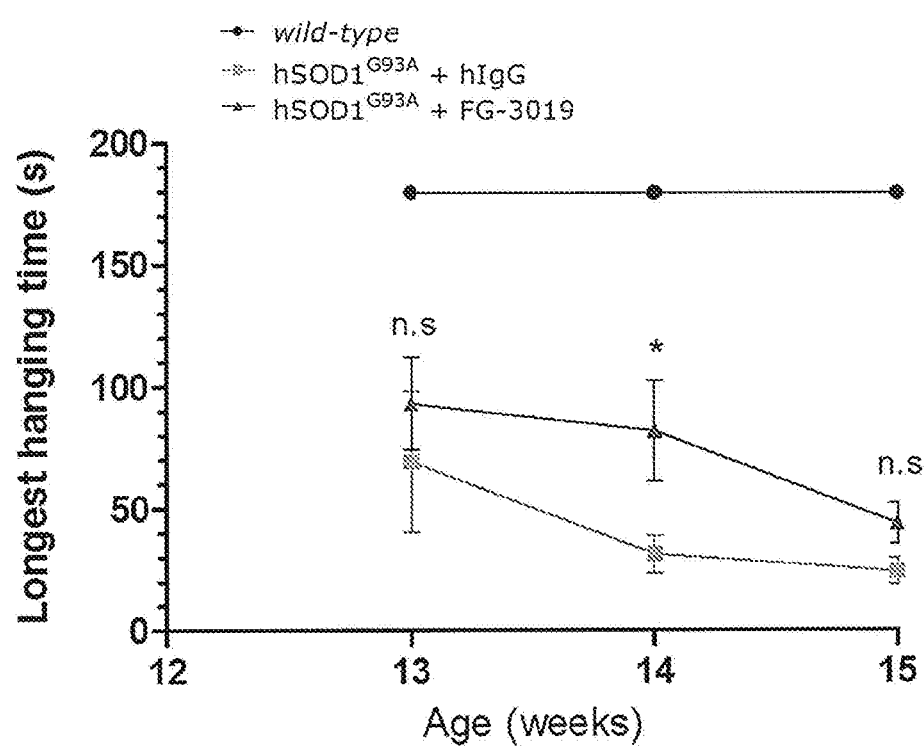
FIG. 8 illustrates the holding time of wild-type and hSOD1$^{G93A}$ mice in a two limb hanging test. Individual mice were tested three times and the longest time plotted. In each trial, wild-type mice were able to grip a wire strand for the entire 180 second test period, n=8. hSOD1$^{G93A}$ mice treated with huIgG were weaker at 13 weeks of age with a mean hanging time of 69.6±29.0 seconds that diminished by week 15 to 24.4±5.4 seconds, n=5. Treatment with FG-3019 enabled hSOD1$^{G93A}$ mice to hang on the wire for 93.4±18.8 seconds at 13 weeks that diminished by week 15 to 44.0±8.4 seconds at with and, n=7. The difference at week 14 between hSOD1$^{G93A}$ mice treated with huIgG or FG-3019 was statistically significant, p<0.05. These results demonstrate that treatment with an anti-CTGF agent preserves muscle strength and reduces the rate at which strength is lost in a MND model.

Wild-type and hSOD1$^{G93A}$ mice from Example 1 were tested in a two limb hang test over the course of three weeks starting at age 13 weeks. Mice were timed for their ability to grip a wire strand for a 180 second test period. Timing started when a mouse gripped the wire with both paws and timing stopped when the mouse let go of the wire strand and dropped to the ground. Each mouse was tested three times with the longest hang time for each mouse used in the analysis. All wild-type mice, n=8, were able to grip the wire for the entire 180 second time period, FIG. 8. In contrast, hSOD1$^{G93A}$ mice treated with huIgG had a mean hanging time of 69.6±29.0 seconds at 13 weeks of age, n=5. Hang time diminished by week 15 to a mean hanging time of 24.4±5.4 seconds. hSOD1$^{G93A}$ mice treated with FG-3019 had a mean hang time of 93.4±18.8 seconds at 13 weeks, n=7. By week 15, hang time diminished to 44.0±8.4 seconds. The results of the hang test demonstrate that treatment with an anti-CTGF agent preserves muscle strength and reduces the rate at which strength is lost in a model of ALS, suggesting that treatment with an anti-CTGF agent may preserve muscle strength in ALS and other MNDs.

Example 8: Inhibition of CTGF Reduces Loss of Locomotor Activity

Figure 9A:
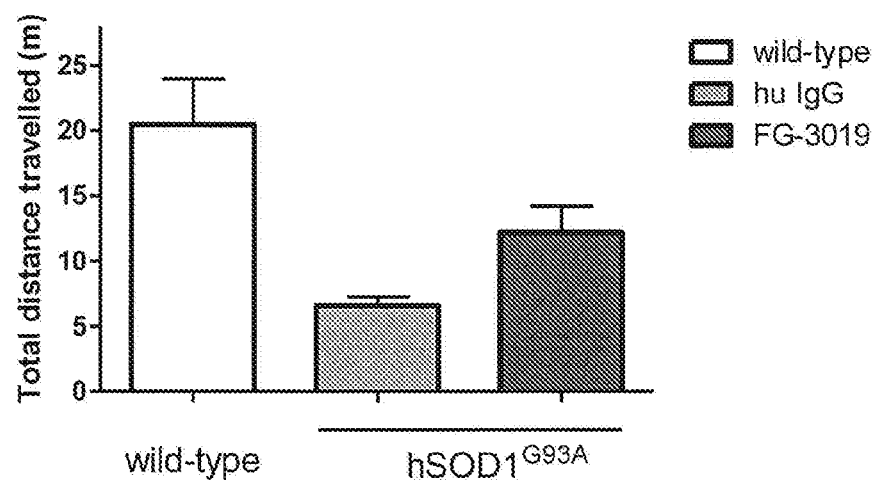
FIGS. 9A and 9B illustrate the degree of locomotor activity of wild-type and hSOD1$^{G93A}$ mice in an open field test.
Figure 9B:
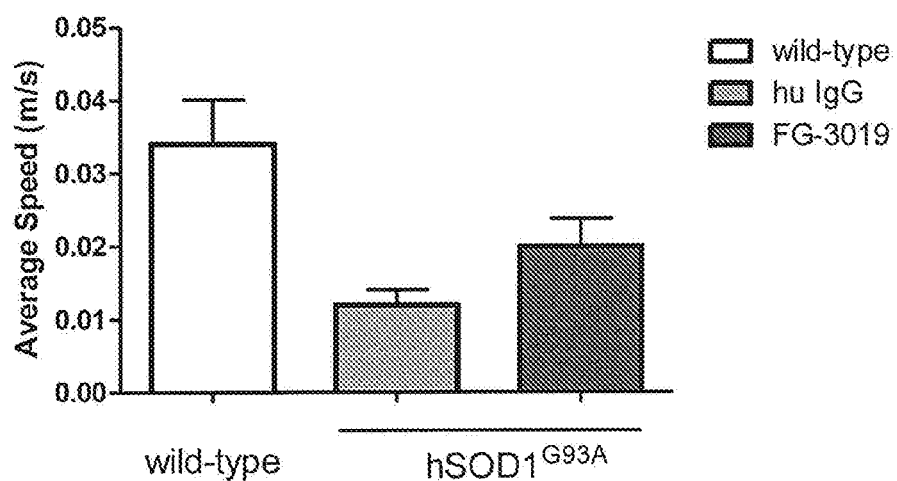

Mice from Example 1 were tested weekly during the course of respective treatments for locomotor activity using an open field test (Gerber Y N, et al. *Front Cell Neurosci.* 7:280 (2013)). Animals were placed in an empty enclosure (40×40 cm) and to avoid behavior bias due to stress, the mice were first acclimated for 2 minutes before their behavior and movements were video recorded for 10 minutes. The videos were analyzed using ANY-maze® software (Stoelting Colo., USA) to measure the total distance travelled. At week 17, wild-type mice traveled approximately 20.5 m with an average speed of about 0.034 m/s. See FIGS. 9A and 9B. In contrast, hSOD1$^{G93A}$ mice treated with huIgG traveled an average of 6.6 m at an average speed of about 0.012 m/s in an open field test. Treatment with FG-3019 improved the average distance traveled of hSOD1$^{G93A}$ mice to about 12.2 m and increased the average speed to 0.020 m/s. N=3. The open field test results demonstrate that inhibition of CTGF reduces the rate of loss of locomotor activity in a model of ALS. These results suggest that the use of an anti-CTGF agent may increase the period of independent living and mobility in subjects with ALS or other MNDs by slowing the rate at which muscle weakness develops.

In sum, the results described above demonstrated that methods and agents of the invention were effective at maintaining body weight and reducing the hallmarks of muscle fibrosis, i.e., the pathological expression and deposition of ECM components (fibronectin, collagen I and total collagen) in an animal model of ALS. Further, these results show that methods and agents of the invention were effective for reducing muscle fibrosis and muscle damage, while preserving muscle strength and locomotor activity. These findings predict that inhibition of CTGF, using the methods and agents of the invention, will provide an effective treatment for ALS and other MNDs.

Various modifications of the invention, in addition to those shown and described herein, will become apparent to those skilled in the art from the foregoing description. Such modifications are intended to fall within the scope of the appended claims.

All references cited herein are hereby incorporated by reference herein in their entirety.

What is claimed is:

1. A method of ameliorating weight loss of a subject with amyotrophic lateral sclerosis (ALS), the method comprising administering to a subject in need thereof an effective amount of an anti-CTGF antibody that has the same amino acid sequence as the antibody produced by the cell line identified by ATCC Accession No. PTA-6006, thereby ameliorating the subject with ALS loss of weight.

2. A method of reducing muscle atrophy of a subject with amyotrophic lateral sclerosis (ALS), the method comprising administering to a subject in need thereof an effective amount of an anti-CTGF antibody that has the same amino acid sequence as the antibody produced by the cell line identified by ATCC Accession No. PTA-6006, thereby reducing muscle atrophy of the subject with ALS.

3. A method of preserving muscle strength of a subject with amyotrophic lateral sclerosis (ALS), the method comprising administering to a subject in need thereof an effective amount of an anti-CTGF antibody that has the same amino acid sequence as the antibody produced by the cell line identified by ATCC Accession No. PTA-6006, thereby preserving muscle strength of the subject with ALS.

4. A method of reducing nerve demyelination of a subject with amyotrophic lateral sclerosis (ALS), the method comprising administering to a subject in need thereof an effective amount of an anti-CTGF antibody that has the same amino acid sequence as the antibody produced by the cell line identified by ATCC Accession No. PTA-6006, thereby reducing nerve demyelination of the subject with ALS.

5. A method of reducing disease progression of a subject with amyotrophic lateral sclerosis (ALS), the method comprising administering to a subject in need thereof an effective amount of an anti-CTGF antibody that has the same amino acid sequence as the antibody produced by the cell line identified by ATCC Accession No. PTA-6006, thereby reducing disease progression of the subject with ALS.

6. A method of reducing loss of movement of a subject with amyotrophic lateral sclerosis (ALS), the method comprising administering to a subject in need thereof an effective amount of an anti-CTGF antibody that has the same amino acid sequence as the antibody produced by the cell line identified by ATCC Accession No. PTA-6006, thereby reducing loss of movement of the subject with ALS.

7. The method of any one of claims 1-6, wherein the effective amount of the anti-CTGF antibody is at least 10 mg/kg.

8. The method of claim 7, further comprising the administration of riluzole.

* * * * *